(12) United States Patent
Zhang et al.

(10) Patent No.: US 9,157,908 B2
(45) Date of Patent: Oct. 13, 2015

(54) CHITOSAN-ALGINATE SCAFFOLD CELL CULTURE SYSTEM AND RELATED METHODS

(75) Inventors: Miqin Zhang, Bothell, WA (US); Forrest Kievit, Brier, WA (US); Matthew Chi-hang Leung, Seattle, WA (US); Stephen Florczyk, Gaithersburg, MD (US)

(73) Assignee: University of Washington through its Center for Commercialization, Seattle, WA (US)

( * ) Notice: Subject to any disclaimer, the term of this patent is extended or adjusted under 35 U.S.C. 154(b) by 548 days.

(21) Appl. No.: 13/453,672

(22) Filed: Apr. 23, 2012

(65) Prior Publication Data

US 2012/0272347 A1    Oct. 25, 2012

Related U.S. Application Data

(60) Provisional application No. 61/478,429, filed on Apr. 22, 2011.

(51) Int. Cl.
| | | |
|---|---|---|
| *C12Q 1/18* | (2006.01) | |
| *A61K 49/00* | (2006.01) | |
| *G01N 33/50* | (2006.01) | |
| *C12N 5/09* | (2010.01) | |

(52) U.S. Cl.
CPC .......... *G01N 33/5082* (2013.01); *C12N 5/0693* (2013.01); *G01N 33/5011* (2013.01); *C12N 2513/00* (2013.01); *C12N 2533/72* (2013.01); *C12N 2533/74* (2013.01)

(58) Field of Classification Search
IPC ............ G01N 33/5082,33/5011; C12N 5/0693, C12N 2513/00
See application file for complete search history.

(56) References Cited

U.S. PATENT DOCUMENTS

| | | | |
|---|---|---|---|
| 5,830,493 A | 11/1998 | Yokota | |
| 5,836,970 A | 11/1998 | Pandit | |
| 5,888,987 A | 3/1999 | Haynes | |
| 6,027,744 A | 2/2000 | Vacanti | |
| 6,096,344 A * | 8/2000 | Liu et al. | 424/501 |
| 6,150,581 A | 11/2000 | Jiang | |
| 6,171,340 B1 | 1/2001 | McDowell | |
| 6,207,218 B1 | 3/2001 | Layrolle | |
| 6,699,848 B1 | 3/2004 | Barbeau | |
| 6,836,970 B2 | 1/2005 | Hirano | |
| 7,736,669 B2 | 6/2010 | Zhang | |
| 7,754,479 B2 | 7/2010 | Han | |
| 8,147,858 B2 | 4/2012 | Zhang | |
| 8,349,804 B2 | 1/2013 | Park | |
| 8,460,692 B2 | 6/2013 | Zhang | |
| 8,568,659 B2 * | 10/2013 | Lee | 422/50 |
| 8,609,133 B2 | 12/2013 | Zhang | |
| 2002/0039567 A1 | 4/2002 | Wallimann | |
| 2004/0044408 A1 | 3/2004 | Hungerford | |
| 2005/0118230 A1 | 6/2005 | Hill | |
| 2006/0115511 A1 | 6/2006 | Zhang | |
| 2006/0205071 A1 | 9/2006 | Hasson | |
| 2006/0251613 A1 | 11/2006 | Zhang | |
| 2007/0160681 A1 | 7/2007 | Park | |
| 2008/0242850 A1 | 10/2008 | Kim | |
| 2008/0294407 A1 | 11/2008 | Siegelmann | |
| 2009/0130701 A1 | 5/2009 | Ho | |
| 2010/0062949 A1 * | 3/2010 | Lee | 506/12 |
| 2010/0196337 A1 | 8/2010 | Perry | |
| 2010/0234863 A1 | 9/2010 | Zhang | |
| 2011/0071254 A1 | 3/2011 | Zhang | |
| 2011/0244501 A1 | 10/2011 | Chu | |
| 2012/0272347 A1 | 10/2012 | Zhang | |

FOREIGN PATENT DOCUMENTS

| | | | | |
|---|---|---|---|---|
| WO | 2006/101453 A1 | 9/2006 | | |
| WO | 2007/046775 A1 | 4/2007 | | |
| WO | WO 2013/155114 A1 * | 4/2011 | ............. | A61L 27/56 |
| WO | 2011/133599 A2 | 10/2011 | | |
| WO | 2011/151225 A1 | 12/2011 | | |
| WO | 2011/154552 A1 | 12/2011 | | |
| WO | 2011/163551 A2 | 12/2011 | | |
| WO | 2013/155114 A1 | 10/2013 | | |

OTHER PUBLICATIONS

Tsoy et al. Biochem Supplement Series B:Biochemical Chemistry (Sep. 2010) 4(3):243-250; abstract only.*
Adekogbe, I., and A. Ghanem "Fabrication and Characterization of DTBP-Crosslinked Chitosan Scaffolds for Skin Tissue Engineering," Biomaterials 26(35):7241-7250, Dec. 2005.
Agrawal, P., et al., "Chitosan-Based Systems for Molecular Imaging," Advanced Drug Delivery Reviews 62(1):42-58, Jan. 2010.
Alves, N.M., and J.F. Mano, "Chitosan Derivatives Obtained by Chemical Modifications for Biomedical and Environmental Applications," International Journal of Biological Macromolecules 43(5):401-414, Dec. 2008.
Amidi, M., and W.E. Hennink, "Chitosan-Based Formulations of Drugs, Imaging Agents and Biotherapeutics," Advanced Drug Delivery Reviews 62(1)1-2, Jan. 2010.

(Continued)

*Primary Examiner* — Marcia S Noble
(74) *Attorney, Agent, or Firm* — Christensen O'Connor Johnson Kindness PLLC

(57) ABSTRACT

Methods for culturing cancer cells in vitro using a three-dimensional scaffold, scaffolds that include the cultured cancer cells, and methods for using the cultured cancer cells and the scaffolds that include the cultured cancer cells in anticancer therapeutic drug development.

12 Claims, 17 Drawing Sheets

(56) References Cited

OTHER PUBLICATIONS

Bhattarai, N., et al., "Chitosan-Based Hydrogels for Controlled, Localized Drug Delivery," Advanced Drug Delivery Reviews 62(1):63-99, Jan. 2010.

Bhattarai, N., et al., "Electrospun Chitosan-Based Nanofibers and Their Cellular Compatibility," Biomaterials 26(31)15176-6184, Nov. 2005.

BI, L., et al., "Reconstruction of Goat Tibial Defects Using an Injectable Tricalcium Phosphate/Chitosan in Combination with Autologous Platelet-Rich Plasma," Biomaterials 31(12):3201-3211, Apr. 2010.

Brandl, F., et al., "Rational Design of Hydrogels for Tissue Engineering: Impact of Physical Factors on Cell Behavior," Biomaterials 28(2):134-146, Jan. 2007.

Chatterjee, K., et al., "The Effect of 3D Hydrogel Scaffold Modulus on Osteoblast Differentiation and Mineralization Revealed by Combinatorial Screening," Biomaterials 31(19):5051-5062, Jul. 2010.

Chen, J.D., et al., "Corrigendum to: In Situ Fabrication of Nano-Hydroxyapatite in a Macroporous Chitosan Scaffold for Tissue Engineering," Journal of Biomaterials Science 21(3):413, Apr. 2012.

Chiang, T.-Y., et al., "Physicochemical Properties and Biocompatibility of Chitosan Oligosaccharide/Gelatin/Calcium Phosphate Hybrid Cements," Materials Chemistry and Physics 120(2-3):282-288, Apr. 2010.

Chicatun, F. et al., "Osteoid-Mimicking Dense Collagen/Chitosan Hybrid Gels," Biomacromolecules 12(8):2946-2956, Aug. 2011.

Collins, A.M., et al., "Bone-Like Resorbable Silk-Based Scaffolds for Load-Bearin Osteoregenerative Applications," Advanced Materials 21(1):75-78, Jan. 2009.

Dado, D., and S. Levenberg, "Cell-Scaffold Mechanical Interplay Within Engineered Tissue," Seminars in Cell & Developmental Biology 20(6):656-664, Aug. 2009.

Di Martino, A., et al., "Chitosan: A Versatile Biopolymer or Orthopaedic-Tissue-Engineering," Biomaterials 26(30):5983-5990, Oct. 2005.

Dumas, V., et al., "The Effect of Dual Frequency Cyclic Compression on Matrix Deposition by Osteoblast-Like Cells Grown in 3D Scaffolds and on Modulation of VEGF Variant Expression," Biomaterials 30(19):3279-3288, Jul. 2009.

Elizalde-Peña, E.A., et al., "Synthesis and Characterization of Chitosan-g-glycidyl Methacrylate With Methyl Methacrylate," European Polymer Journal 43(9):3903-3969, Sep. 2007.

Engler, A.J., et al., "Matrix Elasticity Directs Stem Cell Lineage Specification," Cell 126(4):677-689, Aug. 2006.

Fleury C., et al. "Effect of Cobalt and Chromium Ions on Human MG-63 Osteoblasts In Vitro: Morphology, Cytotoxicity, and Oxidative Stress," Biomaterials 27(18):3351-3360, Jun. 2006.

Jayakumar, R., et al., "Novel Chitin and Chitosan Nariofibers in Biomedical Applications," Biotechnology Advances 28(1):142-150, Jan.-Feb. 2010.

Jiang, L., et al., "Preparation and Biological Properties of a Novel Composite Scaffold of Nano-Hydroxyapatite/Chitosan/Carboxymethyl Cellulose for Bone Tissue Engineering," Journal of Biomedical Science 16:65, Jul. 2009.

Jiang, L., et al., "Preparation and Properties of Nano-Hydroxyapatite/Chitosan/Carboxymethyl Cellulose Composite Scaffold," Carbohydrate Polymers 74(3-4):680-684, Nov. 2008.

Jiang, T., et al., "In Vitro Evaluation of Chitosan/Poly(Lactic Acid-Glycolic Acid) Sintered Microsphere Scaffolds for Bone Tissue Engineering," Biomaterials 27(28):4894-4903, Oct. 2006.

Kaur, G., et al., "The Promotion of Osteoblastic Differentiation of Rat Bone Marrow Stromal Cells by a Polyvalent Plant Mosaic Virus," Biomateriais 29(30):4074-4081, Oct. 2008.

Kaur, G., et al., "Regulation of Osteogenic Differentiation of Rat Bone Marrow Stromal Cells on 2D Nanorod Substrates," Biomaterials 31(7):1732-1741, Mar. 2010.

Kean, T., and M. Thanou, "Biodegradation, Biodistribution and Toxicity of Chitosan," Advanced Drug Delivery Reviews 62(1):3-11, Jan. 2010.

Kim. I,-Y., et al., "Chitosan and Its Derivatives for Tissue Engineering Applications" Biotechnology Advances 26(1):1-21, Jan.-Feb. 2008.

Lee, K.Y., et al., "Electrospinning of Polysaccharides for Regenerative Medicine" Advanced Drug Delivery Reviews 61(12):1020-1032, Oct. 2009.

Li, Z., et al., "Chitosan—Alginate Hybrid Scaffolds for Bone Tissue Engineering," Biomaterials 26(18):3919-3928, Jun. 2005.

Liu, H.-C. et al., "Preparation of PLLA Membranes With Different Morphologies for Culture of MG-63 Cells" Biomaterials 25(18):4047-4056, Aug. 2004.

Martins, A.M., et al., "Responsive and In Situ-Forming Chitosan Scaffolds for Bone Tissue Engineering Applications: An Overview of the Last Decade," Journal of Materials Chemistry 20(9):1638-1645, Mar. 2010.

Nguyen, D.A., and H.S. Fogler, "Facilitated Diffusion in the Dissolution of Carboxylic Polymers," AIChE Journal 51(2):415-425, Feb. 2005.

Oliveira, J.M. et al., "Novel Hydroxyapatite/Chitosan Bilayered Scaffold for Osteochondral Tissue-Engineering Applications: Scaffold Design and Its Performance When Seeded With Goat Bone Marrow Stromal Cells," Biomaterials 27(36):6123-6137, Dec. 2006.

Pillai, C.K.S., et al., "Chitin and Chitosan Polymers: Chemistry, Solubility and Fiber Formation," Progress in Polymer Science 34(7):641-678, Jul. 2009.

Rinaudo, M., et al., "Influence of Acetic Acid Concentration on the Solubilization of Chitosan," Polymer 40(25):7029-7032, Dec. 1999.

Seunarine, K., et al., "3D Polymer Scaffolds for Tissue Engineering," Nanomedicine 1(3):281-296, Oct. 2006.

Shanmugasundaram, N., et al., "Collagen—Chitosan Polymeric Scaffolds for the In Vitro Culture of Human Epidermoid Carcinoma Cells," Biomaterials 22(14):1943-1951, Jul. 2001.

Subramanian, A., and H.-Y. Lin, "Crosslinked Chitosan: Its Physical Properties and the Effects of Matrix Stiffness on Chondrocyte Cell Morphology and Proliferation," Journal of Biomedical Material Research Part A 75(3):742-753, Dec. 2005.

Venkatesan, J., and S.-K. Kim, "Chitosan Composites for Bone Tissue Engineering—An Overview," Marine Drugs 8(8):2252-2266, Aug. 2010.

Wang, B., et al., "Focal Adhesion Kinase Signaling Pathway Is Involved in Mechanotransduction in MG-63 Cells," Biochemical and Biophysical Research Communications 410(3):671-676, Jul. 2011.

Yang, S., et al., "The Design of Scaffolds for Use in Tissue Engineering: Part I. Traditional Factors," Tissue Engineering 7(6):679-689, Dec. 2001.

Yang, X., et al., "Acceleration of Osteogenic Differentiation of Preosteoblastic Cells by Chitosan Containing Nanofibrous Scaffolds," Biomacromolecules 10(10):2772-2778, Oct. 2009.

Zhang, Y., and M. Zhang, "Microstructural and Mechanical Characterization of Chitosan Scaffolds Reinforced by Calcium Phosphates," Journal of Non-Crystalline Solids 282(2-3):159-164, Apr. 2001.

Madihally, S.V., and H.W.T. Matthew, "Porous Chitosan Scafolds for Tissue Engineering," Biomaterials 20(12):1133-1142, Jun. 1999.

Nwe N., et al., "The Mechanical and Biological Properties of Chitosan Scaffolds for Tissue Regeneration Templates are Significantly Enhanced by Chitosan from *Gonronella butieri*," Materials 2:314-398, Apr. 2009.

Gooier, A.F., et al., "Engineered Microenvironments for Human Stem Cells," Birth Defects Research. Part C, Embryo Today: Reviews 84(4):335-347, Dec. 2008.

Gombotz, W.R., and S. Wee, "Protein Release From Alginate Matrices," Advanced Drug Delivery Reviews 31(3):267-285, May 1998.

Gligala, Z., and S. Gogolewski, "In Vitro Growth and Activity of Primary Chondrocytes on a Resorbable Polyactide Three-Dimensional Scaffold," Journal of Biomedical Materials Research 49(2):183-191, Feb. 2000.

Guilak, F., et al., "Control of Stem Cell Fate by Physical Interactrorss With the Extracellular Matrix," Cell Stem Cell 5(1):17-26, Jul. 2009.

(56) References Cited

OTHER PUBLICATIONS

Gupta, P.B., et al., "Stochastic State Transitions Give Rise to Phenotypic Equilibrium in Populations of Cancer Cells," Cell 146(4):633-644, Aug. 2011.
Gutowska, A., et al., "Injectable Gels for Tissue Engineering," Anatomical Record 263(4):342-349, Aug. 2001.
Hambley, T.W., and W.N. Hait, "Is Anticancer Drug Development Heading in the Right Direction?" Cancer Research 69:1259-1262. Feb. 2009.
Hari, P.R., et al., "Chilosan/Calcium-Alginate Beads for Oral Delivery of Insulin," Journal of Applied Polymer Science 59(11):1795-1801, Mar. 1996.
Häuselmann, J.H., et al., "Synthesis and Turnover of Proteoglycans by Human and Bovine Adult Articular Chondrocytes Cultured in Alginate Beads," Matrix 12(2):116-129, Apr. 1992.
Hench, L.L. and J. Wilson, "Surface-Active Biomaterials," Science 226(4675):630-636, Nov. 1984.
Hennessy, M., and J.P. Spiers, "A Primer on the Mechanics of P-Glycoprotein the Multidrug Transporter," Pharmacological Research 55(1).1-15, Jan. 2007.
Hirano, S., et al., "Chitosan as an Ingredient for Domestic Animal Feeds," Journal of Agricultural and Food Chemistry 38(5):1214-1217, May 1990.
Hirschhaeuser, F., et al,, "Multicellular Tumor Spheroids: An Underestimated Tool Is Catching up Again," Journal of Biotechnology 148(1):3-15, Jul. 2010.
Hoelzinger, D.B , et al., "Autocrine Factors That Sustain Glioma Invasion and Paracrine Biology in the Brain Microenvironment," Journal of the National Cancer Institute 99(21):1583-1593, Nov. 2007.
Hoffman, L.M., and M.K. Carpenter, "Characterization and Culture of Human Embryonic Stem Cells," Nature: Biotechnology 23(6):699-708, Jun. 2005.
Homicz, M.R., et al., "Human Septal Chondrocyte Redifferentiation in Alginate, Polyglycolic Acid Scaffold, and Monolayer Culture," Laryngoscope 113(1):25-32, Jan. 2003.
Horning J.L , et al., "3-D Tumor Model for In Vitro Emaluation of Anticancer Drugs," Molecular Pharmaceutics 5(5):849-862, Sep.-Oct. 2008.
Huber, M.A., et al., "Molecular Requirements for Epithelial-Meserichymal Transition During Tumor Progression," Current Opinion in Cell Biology 17(5):548-558, Oct. 2005.
Hunziker, E.B., "Articular Cartilage Repair: Basic Science and Clinical Progress. A Review of the Current Status and Prospects," Osteoarthritis and Cartilage 10(6):432-463, Jun. 2002.
Hutmacher, D.W., et al., "An Introduction to Biodegradable Materials for Tissue Engineering Applications," Annals of the Academy of Medicine, Singapore 30(2):183-191, Mar. 2001.
Ikushima, H., et al., "Autocrine TGF-Beta Signaling Maintains Tumorigenicity of Glioma-Initiating Cells Through Sry-Related HMG-Box Factors," Cell Stem Cell 5(5):504-514, Nov. 2009.
International Search Report and Written Opinion mailed Jul. 5, 2013, issued in International Patent Application No. PCT/US2013/035848, filed Apr. 9, 2013, 11 pages.
Jarcho, M., "Calcium Phosphate Ceramics as Hard Tissue Prosthetics," Clinical Orthopaedics and Related Research 157:259-278, Jun. 1981.
Jiang, W., et al., "In Vitro Derivation of Functional Insulin-Producing Cells From Human Embryonic Stem Cells," Cell Research 17(4):333-344, Apr. 2007.
Jin, X., et al., "Frizzled 4 Regulates Sternness and Invasiveness of Migrating Glioma Cells Established by Serial Intracranial Transplantation," Cancer Research 71(8):3066-3075, Apr. 2011.
Jouanneau, E., "Angiogenesis and Gliomas: Current Issues and Development of Surrogate Markers," Neurosurgery 62(1):31-50 [discussion 2], Jan. 2008.
Jurisicova, A., et al., "Molecular Requirements for Doxorubicin-mediated Death in Murine Oocytes," Cell Death and Differentiation 13(9):1466-1474, Sep. 2006.

Kelly, S.E., et al., "Rapid Selection and Proliferation of Cd133•Cells From Cancer Cell Lines: Chemotherapeutic Implications," PLoS One 5(4):e10035, pp. 1-18, Apr. 2010.
Kerbel, R.S., "Tumor Angiogenesis," New England Journal of Medicine 358(19):2039-2049, May 2008.
Kerr, C.L., et al., "Expression of Pluripotent Stem Cell Markers in the Human Fetal Ovary," Human Reproduction 23(3):589-599, Mar. 2008.
Khalid, M.N., et al., "Water State Characterization, Swelling Behavior, Thermal and Mechanical Properties of Chitosan Based Networks," European Journal of Pharmaceutical Sciences 15(5):425-432, Jun. 2002.
Kievit, P.M., et al., "Chitosan-Alginate 3D Scaffolds as a Mimic of the Glioma Tumor Microenvironment," Biomaterials 31(22):5903-5910, Aug. 2010.
Kievit, F.M., et al., "Proliferation and Enrichment of CD 133•Glioblastoma Cancer Stem Cells on 3D Chitosan-Alginale Scaffolds," Biomaterials 35(33):9131-9143, Nov. 2014.
Kim, B.-S., and D.J. Mooney, "Development of Biocompatible Synthetic Extracellular Matrices for Tissue Engineering," Trends in Biotechnology 16(5):224-230, Dec. 1998.
Kim, H.J., "Polyelectrolyte Complex Composed of Chitosan and Sodium Alginate for Wound Dressing Application," Journal of Biomaterials Science Polymer Edition 10(5):543-556, 1999.
Kim, S.E., et al., "Porous Chitosan Scaffold Containing Microspheres Loaded With Transforming Growth Factor-Beta1: Implications for Cartilage Tissue Engineering," Journal of Controlled Release 91(3):365-374, Sep. 2003.
Kisiday, J., et al., "Self-Assembling Peptide Hydrogel Fosters Chondrocyte Extracellular Matrix Production and Cell Division: Implications for Cartiiage Tissue Repair," Proceedings of the National Academy of Sciences, USA 99(15):9996-10001, Jul. 2002.
Klokkevold, P.R., et al., "Osteogenesis Enhanced by Chitosan (poly-N-acetyl glucosaminoglycan) In Vitro," Journal of Periodontology 67(11):1170-1175, Nov. 1996.
Kondo, T., et al., "Persistence of a Small Subpopulation of Cancer Stem-Like Cells in the C6 Glioma Cell Line," Proceedings of the National Academy of Sciences USA 101(3):781-786, Jan. 2004.
Kosher, R. A., and R.L. Church, "Stimulation of In Vitro Somite Chondrogenesis by Procollagen and Collagen," Nature 258(5533):327-330, Nov. 1975.
Kosher, R.A., et al., "Environmental Enhancement of In Vitro Chondrogenesis. IV. Stimulation of Somite Chondrogenesis by Exogenous Chondromucoprotein," Developmental Biology 35(2):210-220, Dec. 1973.
Koyano, T., et al., "Attachment and Growth of Cultured Fibroblast Cells on PVA/Chitosan-Blended Hydrogels," Journal of Biomedical Materials Research 39(3):486-490, Mar. 1998.
Kumar, M.N.V.R., "A Review of Chitin and Chitosan Applications," Reactive and Funtional Polymers 46(1):1-27, Nov. 2000.
Kumar, S., and V.M. Weaver, "Mechanics, Malignancy, and Metastasis: The Force Journey of a Tumor Cell," Cancer Metastasis Reviews 28(1-2):113-127, Jun. 2009.
Lahiji, A., et al., "Chitosan Supports the Expression of Extracellular Matrix Proteins in Human Osteoblasts and Chondrocytes," Journal of Biomedical Materials Research 51(4):586-595, Sep. 2000.
Lai, H.L., et al., "The Preparation and Characterization of Drug-Loaded Alginate and Chitosan Sponges," International Journal of Pharmaceutics 251(1-2):175-181, Jan. 2003.
Lai, J.-P., et al., "Sulfatase 2 Up-Regulates Glypican 3, Promotes Fibroblast Growth Factoar Signaling, and Decreases Survival in Hepatocellular Carcinoma," Hepatology 47(4):1211-1222, Apr. 2008.
Lash, J.W., "Environmental Enhancement of In Vitro Chondrodenesis. 3. The Influence of External Potassium Ions and Chondrogenic Differentiation," Developmentai Biology 35(2):370-375, Dec. 1973.
Lathia, J.D., et al., "Direct In Vivo Evidence of Tumor Propagation by Glioblastoma Cancer Stem Cells," PloS One 6(9):e24807, pp. 1-9, 2011.
Lauffenburger, D.A., and D.V. Schaeffer, "The Matrix Delivers: Gene Therapy and Tissue Engineering Team Up to Speed Bone Regeneration," Nature Medicine 5(7):733-434, Jul. 1999.

(56) References Cited

OTHER PUBLICATIONS

Niklason, L.E., and R.S. Langer, "Advances in Tissue Engineering of Blood Vessels and Other Tissues," Transplant Immunology 5(4):303-306, Dec. 1997.

O'Brien., C.A. et al., "Cancer Stem Cells and Self-Renewal," Clinical Cancer Research 16(12):3113-3120, Jun. 2010.

O'Brien, L.E., et al., "Rac1 Orientates Epithelial Apical Polarity Through Effects on Basolateral Laminin Assembly," Nature: Cell Biology 3(9):831-838, Sep. 2001.

Orive, G., et al., "Biocompatibility of Alginate-poly-L-lysine Microcapsules for Cell Therapy," Biomaterials 27(20):3691-3700, Jul. 2006.

Ouyang, G., et al., "Molecular Signaling of the Epithelial to Mesenchymal Transition in Generating and Maintaining Cancer Stem Cells," Cellular and Molecular Life Sciences 67(15):2605-2618, Aug. 2010.

Overgaard. S., et al., "Immobilization of Hybridoma Cells in Chitosan Alginate Beads," Canadian Journal of Chemical Engineeririg 69(2):439-443, Apr. 1991.

Park, Y.J., et al., "Platelet Derived Growth Factor Releasing Chitosan Sponge for Periodontal Bone Regeneration," Biomaterials 21(2):153-159, Jan. 2000.

Parmar, M., and M. Li, "Early Specification of Doparninergic Phenotype During ES Cell Differentiation," BMC Developmental Biology 7(1):86, Jul. 2007, pp. 1-9.

Patel, K.J., and I.F. Tannock, "The Influence of P-Glycoprotein Expression and Its Inhibitors on the Distribution of Doxorubicin in Breast Tumors," BMC Cancer 9:356, Oct. 2009, pp. 1-10.

Pattabiraman, D.R., and R.A. Weinberg, "Tackling the Cancer Stem Cells—What Challenges Do They Pose?" Nature Reviews: Drug Discovery 13(7):497-512, Jul. 2014.

Perka C., et al., "The Use of Fibrin Beads for Tissue Engineering and Subsequential Transplantation," Tissue Engineering 7(3):359-361, Jun. 2010.

Persidis, A., "Tissue Engineering," Nature: Biotechnology 17(5):508-510, May 1999.

Petersen, O.W., et al., "Interaction With Basement Membrane Serves to Rapidly Distinguish Growth and Differentiation Pattern of Normal and Malignant Human Breast Epithelial Cells," Proceedings of the National Academy of Sciences USA 89(19):9064-9068, Oct. 1992.

Petite, H., et al., "Tissue-Engineered Bone Regeneration," Nature: Biotechnology 18(9):959-963, Sep. 2000.

Phan-Lai, V., et al., "CCL21 and IFNγ Recruit and Activate Tumor Specific T cells in 3D Scaffold Model of Breast Cancer," Anti-Cancer Agents in Medicinal Chemistry 14(2):204-210, Feb. 2014.

Phan-Lai, V., et al., "Three-Dimensional Scaffolds to Evaluate Tumor Associated Fibroblast-Mediated Suppression of Breast Tumor Specific T Cells," Biomacromolecules 14(5):1330-1337, May 2013.

Plaia, T.W., et al., "Characterization of a New NIH-Registered Variant Human Embryonic Stem Cell Line, BG01V: A Tool for Human Embryonic Stem Cell Research," Stem Cells 24(3):531-546, Mar. 2006.

Plate, K.H., et al., "Vascular Endothelial Growth Factor Is a Potential Tumour Angiogenesis Factor in Human Gliomas In Vivo," Nature 359(6398):845-848, Oct. 1992.

Porter, B.D., et al., "Mechanical Properties of a Biodegradable Bone Regeneration Scaffold," Journal of Biomechanical Engineering 122(3):286-288, Jun. 2000.

Potta, S.P., et al., "Functional Characterization and Transcriptome Analysis of Embryonic Stem Cell-Derived Contractile Smooth Muscle Cells," Hypertension 53(2):196-204, Feb. 2009.

Prasitsilp, M., et al., "Cellular Responses to Chitosan In Vitro: the Importance of Deacetylation," Journal of Materials Science: Materials in Medicine 11(12):773-778, Dec. 2000.

Presta, M., et al., "Fibroblast Growth Factor/Fibroblast Growth Factor Receptor System in Angiogenesis," Cytokine and Growth Factor Reviews 16(2):159-178, Apr. 2005.

Rao, W., et al., "Enhanced Enrichment of Prostate Cancer Stem-Like Cells With Miniaturized 3D Culture in Liquid Core-Hydrogel Shell Microcapsules," Biomaterials 35(27):7762-7773, Sep. 2014.

Ricci-Vitiani, I., et al., "Tumour Vascularization via Endothelial Differentiation of Glioblastoma Stem-Like Cells," Nature 468(7325):824-828, Dec. 2010.

Rizzo, P., et al., "Cross-Talk Between Notch and the Estrogen Receptor in Breast Cancer Suggests Novel Therapeutic Approaches," Cancer Research 63(13):5226-5235, Jul. 2008.

Rosen, J.M., and C.T. Jordan, "The Increasing Complexity of the Cancer Stem Cell Paradigm," Science 324(5935):1670-1673, Jun. 2009.

Saito, N., et al., "A Biodegradable Polymer as a Cytokine Delivery System for Inducing Bone Formation," Nature: Biotechnology 19(4):332-335, Apr. 2001.

Sangro, B., "Refined Tools for the Treatment of Hepatocellular Carcinoma," Journal of Hepatology 42(5):629-631, May 2005.

Savant, V.D., and J.A. Torres, "Protein Adsorption on Chitosan-Polyanion Complexes: Application to Aqueous Food Processing Wastes," in H. Chen and C. Weller (eds.), "Structure and Functionality of Biopolymers," pp. 537-542, 2001.

Schoonen, W.G.E.J., et al., "Cytotoxic Effects of 110 Reference Compounds on HepG2 Cells and for 60 Compounds on HeLa, ECC-1 and CHO Cells: II Mechanistic Assays on NAD(P)H, ATP and DNA Contents," Toxicology In Vitro 19(4):491-503, Jun. 2005.

Schulze, M., et al., "Adult Human Chondrocytes in Alginate Culture. Preservation of the Phenotype for Further Use in Transplantation Models," Der Orthopäde 29(2):100-106, Feb. 2000.

Sechriest, V.F., et al., "GAG-Augmented Polysaccharide Hydrogel: A Novel Biocompatible and Biodegradable Material to Support Chondrogenesis," Journal of Biomedical Materials Research 49(4):534-541, Mar. 2000.

Sermeus, A., et al., "Hypoxia Induces Protection Against Etoposide-Induced Apoptosis: Molecular Profiling of Changes in Gene Expression and Transcription Factor Activity," Molecular Cancer 7:27, Mar. 2008, pp. 1-18.

Service, R.F., "Tissue Engineers Build New Bone," Science 289(5484):1498-1500, Sep. 2000.

Shanmugasundaram, N., et al., "Collagen-Chitosan Polymeric Scaffolds for the In Vitro Culture of Human Epidermoid Carcinoma Cells," Biomaterials 22(14):1943-1951, Jun. 2001.

Shen, G., et al., "Identification of Cancer Stem-Like Cells in the C6 Glioma Cell Line and the Limitation of Current Identification Methods," In Vitro Cellular and Developmental Biology: Animal 44(7):280-289, Jul.-Aug. 2008.

Shirakawa, H., et al., "Glypican-3 Expression Is Correlated With Poor Prognosis in Hepatocellular Carcinoma," Cancer Science 100(8):1403-1407, Aug. 2009.

Shiraki, N., et al., "Differentiation of Mouse and Human Embryonic Stem Cells Into Hepatic Lineages," Genes to Cells 13(7):731-746, Jul. 2008.

Singh, S.K., et al., "Identification of Human Brain Tumour Initiating Cell," Nature 432(7015):396-401, Nov. 2004.

Sittinger, M., et al., "Resorbable Polyesters in Cartilage Engineering: Affinity and Biocompatibility of Polymer Fiber Structures to Chondrocytes," Journal of Biomedical Materials Research 33(2):57-63, Summer 1996.

Smalley, K.S., et al., "Life Isn't Flat: Taking Cancer Biology to the Next Dimension," In Vitro Cellular and Developmental Biology: Animal 42(8-9):242-247, Sep.-Oct. 2006.

Smith, B.H., et al., "Three-Dimensional Culture of Mouse Renal Carcinoma Cells in Agarose Macrobeads Selects for a Subpopulation of Cells With Cancer Stem Cell or Cancer Progenitor Properties," Cancer Research 71(3):716-724, Feb. 2011.

Spangenberg, H.C., et al., "Targeted Therapy for Hepatocellular Carcinoma," Nature Reviews: Gastroenterology and Hepatology 6(7):423-432, Jul. 2009.

Stacey, G.N., et al., "The Development of 'Feeder' Cells for the Preparation of Clinical Grade Hes Cell Lines: Challenges and Solutions," Journal of Biotechnology 125(4):583-588, Oct. 2006.

Sugimoto, M., et al., "Preparation and Characterization of Water-Soluble Chitin and Chitosan Derivatives," Carbohydrate Polymers 36(1):49-59, May 1998.

Suh, J.-K., and H.W.T. Matthew, "Application of Chitosan-Based Polysaccharide Biomaterials in Cartilage Tissue Engineering: A Review," Biomaterials 21(24):2589-2598, Dec. 2000.

(56) References Cited

OTHER PUBLICATIONS

Tabata, Y., and Y. Ikada, "Protein Release from Gelatin Matrices," Advanced Drug Delivery Reviews 31(3):287-301, May 1998.
Takahashi, T., et al., "Characteristics of Polyion-Complex of Chitosan With Sodium Alginate and Sodium Polyacrylate," International Journal of Pharmaceutics 61(1-2):35-41, Jun. 1990.
Tamplin. O., et al., "Microarray Analysis of Foxa2 Mutant Mouse Embryos Reveals Novel Gene Expression and Inductive Roles for the Gastrula Organizer and Its Derivatives," BMC Genomics 9(1):511, Oct. 2008, pp. 1-19.
Temenoff, J.S., and A.G. Mikos, "Injectable Biodegradable Materials for Orthopedic Tissue Engineering," Biomaterials 21(23):2405-2412, Dec. 2000.
Laurencin, C.T., et al., "Tissue Engineering: Orthopedic Applications," Annual Review of Biomedical Engineering 1:19-46, 1999.
Lee, C.R., et al., "Effects of a Cultured Autologous Chondrocyte-Seeded Type II Collagen Scaffold on the Healing of a Chondral Defect in a Canine Model," Journal of Orthopaedic Research 21(2):272-281. Mar. 2003.
Lee, D.A., et al., "Expansion of Chondrocytes for Tissue Engineering in Alginate Beads Enhances Chondrocytic Phenotype Compared to Conventional Monolayer Techniques," Acta Orthopaedics Scandinavica 74(1):6-15, Feb. 2003.
Leung, M., et al., "Chitosan-Alginate Scaffold Culture System for Hepatocellular Carcinoma Increases Malignancy and Drug Resistance," Pharmaceutical Research 27(9):1939-1948, Sep. 2010.
Li, J., et al., "Culture of Primary Rat Hepatocytes Within Porous Chitosan Scaffolds," Journal of Biomedical Materials Research Part A 67A(3):938-943, Dec. 2003.
Li, W.-J., et al., "Biological Response of Chondrocytes Cultured in Three-Dimensional Nanofibrous Poly($\epsilon$-caprolactone) Scaffolds," Journal of Biomedical Materials Research Part A 67A(4):1105-1114, Dec. 2005.
Li. Z., and M. Zhang, "Chitosan-Alginate as Scaffolding Material for Cartilage Tissue Engineering," Journal of Biomedical Materials Research A 75(2):485-493, Nov. 2005.
Li, Z., et al., "Chitosan-Alginate Hybrid Scaffolds for Bone Tissue Engineering," Biomaterials 26(18):3919-3928, Jun. 2005.
Li, Z., et al., "Feeder-Free Self-Renewal of Human Embryonic Stem Cells in 3D Porous Natural Polymer Scaffolds," Biomaterials 31(3):404-412, Jan. 2010.
Li, Z., et al., "On-Site Alginate Gelation for Enhanced Cell Proliferation and Uniform Distribution in Porrous Scaffolds," Journal of Biomedical Materials Research Part A 86A(2):552-559, Aug. 2008.
Lin. R.-Z. and H.Y. Chang, "Recent Advances in Three-Dimensional Multicellular Spheroid Culture for Biomedical Research," Biotechnology Journal 3(9-10):1172-1184, Oct. 2008.
Liu, L.-S., et al., "Controlled Release of Interleukin 2 for Tumor Immunotherapy Using Alginate/Chiosan Porous Microspheres," Journal of Controlled Release 43(1):85-74, Jan. 1997.
Liu, N., et al., "Molecular Mechanisms Involved in Self-Renewal and Pluripotency of Embryonic Stem Cells," Journal of Cellular Physiology 211(2):279-286, May 2007.
Llovet, J.M., et al., "Sorafenib in Advanced Hepatocellular Carcinoma," New England Journal of Medicine 359(4):378-390, Jul. 2008.
Lu, H.H., et al., "Three-Dimensional, Bioactive, Biodegradable, Polymer-Bioactive Glass Composite Scaffolds With Improved Mechanical Properties Support Collagen Synthesis and Mineralization of Human Osteoblast-Like Cells in Vitro," Journal of Biomedical Materials Research 64A(3):465-474, Mar. 2003.
Ludwig, T.E., et al., "Derivation of Human Embryonic Stem Cells in Defined Conditions," Nature Biotechnology 24(2):185-187, Feb. 2006.
Ludwig, T.E., et al., "Feeder-Independent Culture of Human Embryon Stem Cells," Nature: Methods 3(8).637-646, Aug. 2006.
Lund, A.W., et al., "The Natural and Engineered 3D Microenvironment as a Regulatory Cue During Stem Cell Fate Determination," Tissue Engineering Part B. Reviews 15(3):311-380, Sep. 2009.
Lutolf M.P., and J.A. Hubbell, "Synthetic Biomaterials as Instructive Extracellular Microenvironments for Morphogenesis in Tissue Engineering," Nature: Biotechnology 2(1):41-7-55, Jan. 2005.
Lutolf, M.P., et al., "Repair of Bone Defects Using Synthetic Mirnetics of Collagenous Extracellular Matrices," Nature: Biotechnology 21(5):513-518, May 2003.
Ma, S., et al., "Identification and Characterization of Tumorigenic Cancer Stem/Progenitor Cells," Gastroenterology 132(7):2542-2556, Jun. 2007.
Madihally, S.V., and H. Matthew, "Porous Chitosan Scaffolds for Tissue Engineeering," Biomaterials 20(12):1133-1142, Jun. 1999.
Malette, W.G., et al., "Chitosan Effect in Vascular Surgery, Tissue Culture and Tissue Regeneration," in R. Muzzarelli et al. (eds.), "Chitin in Nature and Technology," Plenum Press, New York, pp. 435-442, 1986.
Mallein-Gerin, F., et al., "Proteoglycan and Collagen Synthesis Are Correlated With Actin Organization in Dedifferentiating Chondrocytes," European Journal of Cell Biology 56(2):364-373, Dec. 1991.
Mani, S.A., et al., "The Epithelial-Mesenchymal Transition Generates Cells With Properties of Stem Cells," Cell 133(4):704-715, May 2008.
Marijnissen, W.J, et al., "Alginate as a Chondrocyte-Delivery Substance in Combination With a Non Woven Scaffold for Cartilage Tissue Engineering," Biomaterials 23(6):1511-1517, Mar. 2002.
Martin, C., et al., "Acidity Near Eroding Polylactide-Polyolycolide In Vitro and In Vivo in Rabbit Tibial Bone Chambers," Biomaterials 17(24):2373-2380, Dec. 1996.
Mayne, R., et al., "Changes in Type of Collagen Synthesized as Clones of Chick Chondrocytes Grow and Eventually Lose Division Capacity," Proceedings ot the National Academy of Sciences USA 73(5):1674-1678, May 1976.
Meads M.B., et al., "Environment-Mediated Drug Resistance: A Major Contributor to Minimal Residual Disease," Nature Reviews: Cancer 9(9):665-674, Sep. 2009.
Mercer, R.W., et al., "Therapies for Malignant Glioma: Progress and Potential," BioDrugs 23(1):25-35, 2009.
Meyer, M.J., et al., "CD44(pos)CD49f(hi)CD133/2(hi) Defines Xenograft-Initiating Cells in Estrogen Receptor-Negative Breast Cancer," Cancer Research 70(11):4624-4633, Jun. 2010.
Miki, J. et al., "Identification of Putative Stem Cell Markers, CD133 and CXCR4, in hTERT-Immortalized Primary Nonmalignant and Malignant Tumor-Derived Human Prostate Epithelial Cell Lines and in Prostate Cancer Specimens," Cancer Research 67(7):3153-3161, Apr. 2007.
Minchinton, A.I., and I.F. Tannock, "Drug Penetration in Sobel Tumours," Nature Reviews: Cancer (8):583-592, Aug. 2006.
Minuth, W.W., et al., "Tissue Engineering: Generation of Differentiated Artificial Tissues for Biomedical Applications," Cell and Tissue Research 291(1):1-11, Jan. 1998.
Miralles, G., et al., "Sodium Alginate Sponges With or Without Sodium Hyaluronate: In Vitro Engineering of Cartilage," Journal of Biomedical Materials Research 57(2):268-278, Nov. 2001.
Mirimanoff, R.O., et al., "Radiotherapy and Temozolomide for Newly Diagnosed Glioblastoma: Recursive Partitioning Analysis of the EORTC 26981/22981—NCIC CE3 Phase III Randomized Trial," Journal of Clinical Oncology24(16):2563-2569, Jun. 2006.
Misra, S., et al., "Hyaluronan-CD44 Interactions as Potential Targets for Cancer Therapy," FEBS Journal 278(9):1429-1443, May 2011.
Miyazaki, S., et al., "Pharmaceutical Application of Biomedical Polymers. XXIX. Preliminary Study on Film Dosage Form Prepared From Chitosan for Oral Drug Delivery," Acta Pharmaceutica Nordica 2(6):401-406, 1990.
Montanaro, L., et al., "In Vitro Effects on MG63 Osteoblast-Like Cells Following Contact With Two Roughness-Differing Fluorohydroxyapatite-Coated Titanium Alloys," Biomaterials 23(17):3651-3659, Sep. 2002.
Muzzarelli, C., and R.A. Muzzarelli, "Natural and Artificial Chitosan-Inorganic Composites," Journal of Inorganic Biochemistry 92(2):89-94, Nov. 2002.
Muzzarelli, R et al., "Stimulatory Effect on Bone Formation Exerted by a Modified Chitosan," Biomaterials 15(13):1075-1081, Oct. 1994.

(56) References Cited

OTHER PUBLICATIONS

Muzzarelli, R., et al., "Osteoconduction Exerted by Methylpyrrolidinone Chitosan Used in Dental Surgery," Biomaterials 14(1):39-43, 1993.
Muzzarelli, R., et al., "Reconstruction of Parodontal Tissue With Chitosan," Biomaterials 10(9):598-603, Nov. 1989.
Nagy, J.A., et al., "Why Are Tumour Blood Vessels Abnormal and Why Is It Important to Know?" Bntish Journal of Cancer 100(6):865-869, Mar. 2009.
Nassar, A., et al., "Utility of Glypican-3 and Survivin in Differentiating Hepatocellular Carcinoma From Benign and Prenaplastic Hepatic Lesions and Metastatic Carcinomas in Liver Fine-Needle Aspiration Biopsies," Diagnostic Cytopathology 37(9):629-635, Sep. 2009.
Nehrer, S., et al., "Canine Chondrocytes Seeded in Type I and Type II Collagen Implants Investigated in Vitro," Journal of Biomedical Materials Research 38(2):95-104, Summer 1997.
Nehrer, S., et al., "Matrix Collagen Type and Pore Size Influence Behaviour of Seeded Canine Chondrocytes," Biomatenals 18(11):769-776, Jun. 1997.
Nelson, T.J., et al., "CXCR4+/FLK-1+ Biomarkers Select a Cardiepoietc Lineage from Embryonic Stem Cells," Stem Cells 26(6):1464-1473, Jun. 2008.
Nettles, D.L., et al., "Potential Use of Chitosan as a Cell Scaffold Material for Cartilage Tissue Engieering," Tissue Engineering 8(6):1009-1016, Dec. 2002.
Niklason, L. E., "Engineering of Bone Grafts," Nature: Biotechnology 18(9):929-930, Sep. 2000.
Thanoo, B.C., et al., "Cross-Linked Chitosan Microspheres: Preparation and Evaluation as a Matrix for the Controlled Release of Pharmaceuticals," Journal of Pharmacy and Pharmacology 44(4):283-286, Apr. 1992.
Thomson, R C., et al., "Biodegradable Polymer Scaffolds to Regenerate Organs," Advances in Polymer Science 122:245-274, 1995.
Thomson, R.C., et al., "Fabrication of Biodegradable Polymer Scaffolds to Engineer Trabecular Bone," Journal of Biomaterials Science-Polymer Edition 7(1):23-38, 1995.
Toole, B.P., "Hyaluronari-CD44 interactions in Cancer. Paradoxes and Possibilities,"Clinical Cancer Research 15(24):7462-7468, Dec. 2009.
Trédan, O., et al., "Drug Resistance and the Solid Tumor Microenvironment," Journal of the National Cancer Institute 99(19):1441-1454, Oct. 2007.
Ullmann, U., et al., "Epithelial-Mesenchymal Transition Process in Hliman Embryonic Stem Cells Cultured in Feeder-Free Conditions," Molecular Human Reproduction 13(1):21-32, Jan. 2007.
Ushida, T., et al., "Three-Dimensional Seeding of Chondrocytes Encapsulated in Collagen Gel Into PLLA Scaffolds," Cell Transplantation 11(5):489-494, 2002.
Vacholid, L., et al., "Physicochemical Behaviour of Chitin Gels," Carbohydrate Research 28(4):295-304, Jun. 2000.
Van Susante, J.L.C., et al., "Linkage of Chondroitin-Sulfate to Type I Collagen Scaffolds Stimulates the Bioactivity of Seeded Chondrocytes In Vitro," Biomaterials 22(17):2359-2369, Sep. 2001.
Varela, M . et al., "Chemoembolization of Hepatocellular Carcinoma With Drug Eluting Beads: Efficacy and Doxorubicin Pharmacokinetics," Journal of Hepatology 46(3):474-481, Mar. 2007.
Visvader, J.E., and G.J. Lindeman. "Cancer Stem Cells in Solid Tumours: Accumulating Evidence and Unresolved Questions," Nature Reviews: Cancer 8(10):755-768, Oct. 2008.
von der Mark, K., et al., "Relationship Between Cell Shape and Type of Collagen Synthesised as Chondrocytes Lose Their Cartilage Phenotype in Culture," Nature 267(5611):531-532, Jun. 1997.
Wake, M.C., et al., "Pore Morphology Effects on the Fibrovascular Tissue Growth in Porous Polymer Substrates," Cell Transplantation 3(4):339-343, Jul.-Aug. 1994.
Wang, F., et al., "Reciprocal Interactions Between Beta1-Integrin and Epidermal Growth Factor Receptor in Three-Dimensional Basement Membrane Breast Cultures: A Different Perspective in Epithelial Biology," Proceedings of the National Academy of Sciences USA 95(25):14821-14826, Dec. 1998.
Wang, L., et al., "Chitosan-alginate-CaC1(2) System for Membrane Coat Application," Journal of Pharrnaceutical Sciences 90(8):1134-1142, Aug. 2001.
Wang, X.Y., et al., "Glypican-3 Expression in Hepatocellular Tumors: Diagnostic Value for Preneoplastic Lesions and Hepatocellular Carcinomas," Human Pathology 37(11):1435-1441, Nov. 2006.
Waugh, D.J., and C. Wilson, "The Interleukin-8 Pathway in Cancer," Coinical Cancer Research 14(21):6735-6741, Nov. 2008.
Weaver, V.M., et al., "Reversion of the Malignant Phenotype of Human Breast Cells in Three-Dimensional Culture and In Vivo by Integrin Blocking Antibodies," Journal of Cell Biology 137(1):231-245, Apr. 1997.
Westphal, M., and K. Lamszus, "The Neurobiology of Gliomas: From Cell Biology to the Development of Therapeutic Approathes," Nature Reviews: Neuroscience 12(9):495-508, Aug. 2011.
Whang, K., et al., "Engineering Bone Regeneration With Bioabsorbable Scaffolds With Novel Microarchitecture," Tissue Engineering 5(1):35-51, Feb. 1999.
Wichert., A., et al., "Glypican-3 is Involved in Cellular Protection Against Mitoxantrone in Gastric Carcinoma Cells," Oncogene 23(4):945-955, Jan. 2003.
Wu, L., et al., "Experimental Models of Hepatocellular Carcinoma: Developments and Evolution," Journal of Cancer Research and Clinical Oncology 135(8):969-981, Aug. 2009.
Wu, X.Z., et al., "Extracellular Matrix Remodeling in Hepatocellualar Carcinoma: Effects of Soil on Seed?" Medical Hypotheses 66(6):1115-1120, 2006.
Xu, F. and K.J. Burg, "Three-Dimensional Polymeric Systems for Cancer Cell Studies," Cytotechnology 54(3):135-143, Jul. 2007.
Yagi, K., et al., "Effectiveness of Fructose-Modified Chitosan as a Scaffold for Hepatocyte Attachment," Biological and Pharmaceutical Bulletin 20(12):1290-1294, Dec. 1997.
Yamaguchi, H., et al., "Cell Migration in Tumors," Current Opinion in Cell Biology 17(5):559-564, Oct. 2005.
Yan, X.L., et al., "PEC Films Prepared From Chitosan-Alginate Coacervates," Chemical and Pharmaceutical Bulletin 48(7):911-946, Jul. 2000.
Yang, M.-C., et al., "The Cardiomyogenic Differentiation of Rat Mesenchymal Stem Cells on Silk Fibroin-Polysaccharide Cardiac Patches In Vitro," Biomaterials 30(22):3757-3765, Aug. 2009.
Yang, S., et al., "The Design of Scaffolds for Use in Tissue Engineering. Part I Traditional Factors," Tissue Engineering 7(6):679-689, Dec. 2001.
Yang, Y., et al., "Fabrication of Well-Defined PLGA Scaffolds Using Novel Microembossing and Carbon Dioxide Bonding," Biomaterials 26(15):2585-2594, May 2006.
Zeng, X., et al., "BG01V: A Variant Human Embryonic Stem Cell Line Which Exhibits Rapid Growth After Passaging and Reliable Dopaminergic Differentiation," Restorative Neurology and Neuroscience 22(6):421-428, 2004.
Zhang, Q., et al., "Preparation and Characterization of Collagen-Chitosan Composites," Journal of Applied Polymer Science 64(11):2127-2130, Jun. 1997.
Zhang, R., and P.X. MA, "Poly($\alpha$-hydroxyl acids)/Hydroxyapatite Porous Composites for Bone-Tissue Engineering. I. Preparation and Morphology," Journal of Biomedical Materials Research 44(4):446-455, Mar. 1999.
Zhang, Y., and M. Zhang, "Cell Growth and Function on Calcium Phosphate Reinforced Chitosan Scaffolds," Journal of Materials Science: Materials in Medicine 15(3):255-260, Mar. 2004.
Zhang, Y., and M.Q. Zhang, "Calcium Phosphate/Chitosan Composite Scaffolds for Controlled In Vitro Antibiotic Drug Release," Journal of Biomedical Materials Research 62(3):378-386, Dec. 2002.
Zhang, Y. and M.Q. Zhang, "Microstructural and Mechanical Characterization of Chitosan Scaffolds Reinforced by Calcium Phosphates," Journal of Non-Crystalline Solids 282(2-3):159-164, Apr. 2001.

(56) References Cited

OTHER PUBLICATIONS

Zhang, Y., and M.Q. Zhang, "Synthesis and Characterization of Macroporous Chitosan/Calcium Phosphate Composite Scaffolds for Tissue Engineering," Journal of Biomedical Materials Research 55(3):304-312, Jun. 2001.

Zhang, Y., et al., "Calcium Phosphate-Chitosan Composite Scaffolds for Bone Tissue Engineering," Tissue Engineering 9(3):337-345, Apr. 2003.

Zhang, Z., et al., "Pore Size, Tissue Ingrowth, and Endothelialization of Small-Diameter Microporous Polyurethane Vascular Prosthesis," Biomaterials 25(1):177-187, Jan. 2004.

Zhao, R., and G.Q. Daley, "From Fibroblasts to iPS cells: Induced Pluripotency by Defined Factors," Journal of Cellular Biochemistry 105(4):949-955, Nov. 2008.

Zheng, X., et al., "Most C6 Cells Are Cancer Stem Cells: Evidence From Clonal and Population Analyses," Cancer Research 67(8):3691-3697, Apr. 2007.

Zhou, B.B.S., et al., "Tumour-Initiating Cells: Challenges and Opportunities for Anticancer Drug Discovery," Nature Reviews: Drug Discovery 8(10):806-823, Oct. 2009.

Aiba, S., "Studies on Chitosan: 3. Evidence for the Presence of Random and Block Copolymer Structures in Partialiy N-Acetyiated Chitosans," International Journal of Biological Macromolecules 13(1):40-44, Feb. 1991.

Aiedeh, K., et al., "Chitosan Microcapsules as Controlled Release Systems for Insulin," Journal of Microencapsulation 14(5):567-576, Sep.-Oct. 1997.

Aigner, J., et al., "Cartilage Tissue Engineering With Novel Non-woven Structured Biomaterial Based on Hyaluronic Acid Benzyl Ester," Journal of Biomedical Materials Research 42(2):172-181, Nov. 1998.

Andriano, K.P., et al., "In Vitro and In Vivo Comparison of Bulk and Surface Hydrolysis in Absorbable Polymer Scaffolds for Tissue Engineering," Journal of Biomedical Materials Research 48(5):602-612, 1999.

Baguley, B.C., "Multidrug Resistance in Cancer,"Methods in Molecular Biology 596:1 14, 2010.

Becker, T.A., et al., "Calciurn Alginate Gel: A Biocompatible and Mechanically Stable Polymer for Endovascular Embolization," Journal of Biomedical Materials Research 54(1):76-86, Jan. 2001.

Ben-Porath, I., et al., "An Embryonic Stem Cell-Like Gene Expression Signature in Poorly Differentiated Aggressive Human Tumors," Nature: Genetics 40(5):499-507, May 2008.

Benya, P.D., "Modulation and Reexpression of the Chondrocyte Phenotype; Mediation by Cell Shape and Microfilament Modification," Pathology and Immunopathology Research 7(1-2):51-54, 1988.

Benya, P.D., and J.D. Shaffer, "Dedifferentiated Chondrocytes Reexpress the Differentiated Collagen Phenotype When Cultured in Agarose Gels," Cell 30(1):215-224, Aug. 1982.

Bhattarai, N., et al.,"Alginate-Based Nanofibrous Scaffolds: Structural, Mechanical, and Biological Properties," Advanced Materials 18(11):1463-1467, Jun. 2006.

Borovski, T., et al., "Cancer Stem Cell Niche: The Place to Be," Cancer Research 71(3):634-639, Feb. 2011.

Boskey. A.L., "Mineral-Matrix Interactions in Bone and Cartilage," Clinical Orthopaedics and Related Research 281:244-274, Aug. 1992.

Bourguignon, L.Y.W., et al., "Hyaluronan-CD44 Interaction Activates Stem Cell Marker Nanog, Stat-3-Mediated MDR1 Gene Expression, and Ankyrin-Regulated Multidrug Effiux in Breast and Ovarian Tumor Cells," Journal of Biological Chemistry 283(25):17635-17651, Jun. 2008.

Capurro, M., et al., "Glypican-3: A Novel Serum and Histochemical Marker for Hepatocellular Carcinoma," Gastroenterology 125(1):89-97, Jul. 2003.

Caterson, E.J., et al., "Polymer/Alginate Amalgam for Cartilage-Tissue Engineering," Annals of the New York Academy of Sciences 961:134-138, Jun. 2002.

Caterson, E.J., et al., "Three-Dimensional Cartilage Formation by Bone Marrow-Derived Cells Seeded in Polylactide/Alginate Amalgam," Journal of Biomedical Materials Research 57(3):394-403, Dec. 2001.

Chaffer, C.L., et al., "Normal and Neoplastic Nonstem Cells Can Spontaneously Convert to a Stemlike State," Proceedings of the National Academy of Sciences USA 108(19):7950-7955, May 2011.

Chang, M.C., and J. Tanaka, "FT-IR Study for Hydroxyapatite/Collagen Nanocomposite Cross-Linked by Giutaraldehyde," Biomaterials 23(24):4811-4818, Dec. 2002.

Chau, Y., et al., "Antitumor Efficacy of a Novel Polymer-Peptide-Drug Conjugate in Human Tumor Xenograft Models," International Journal of Cancer 118(6):1519-1526, Mar. 2006.

Chen, G., et al., "A Biodegradable Hybrid Sponge Nested With Collagen Microsponges," Journal of Biomedical Materials Research 51(2):273-279, Aug. 2000.

Chen, G., et al., "Hybrid Biomaterials for Tissue Engineering: A Preparative Method for PLA or PLGA—Collagen Hybrid Sponges," Advanced Materials 12(6):455-457, Mar. 2000.

Chen, G.P., et al., "Poly(DL-lactic-co-glycolic acid) Sponge Hybridized With Collagen Microsponges and Deposited Apatite Particulates," Journal of Biomedical Materials Research 57(1):8-14, Oct. 2001.

Chew, J., et al., "A Restricted Cell Population Propagates Glioblastoma Growth After Chemotherapy," Nature 488(7412):522-526, Aug. 2012.

Chu, T.M., et al., "Mechanical and In Vivo Performance of Hydroxyapatite Implants With Controlled Architectures," Biomaterials 23(5):1283-1293, Mar. 2002.

Chung, T.W., et al., "Preparation of Alginate/Galactosylated Chitosan Scaffold for Hepatocyte Attachment," Biomaterials 23(14):2827-2834, Jul. 2002.

Chuu, J.-J., et al., "Effects of Paclitaxel and Doxorubicin in Histocultures of Hepatocellular Carcinomas," Journal of Biomedical Sciences 14(2):233-244, Mar. 2007.

Clement, V., et al., "Hedgehog-GLI1 Signaling Regulates Human Glioma Growth, Cancer Stem Cell Self-Renewal, and Turnongenicity," Current Biology 17(2):165-172, Jan. 2007.

Collins, A.T., et al., "Prospective Identification of Tumorigenic Prostate Cancer Stem Cells," Cancer Research 65(23):10946-10951, Dec. 2005.

Coppi, G., et al., "Chitosan-Alginate Microparticles as a Protein Carrier," Drug Development and Industrial Pharmacy 27(5):393-400, May 2001.

Cretu, A. et al., "Human and Rat Glioma Growth, Invasion, and Vascularization in a Novel Chick Embryo Brain Tumor Model," Clinical & Experimental Metastasis 22(3):225-236, 2005.

Croft, D.R., et al., "Conditional ROCK Activation In Vivo Induces Tumor Cell Dissemination and Angiogenesis," Cancer Research 64(24):8994-9001, Dec. 2004.

Daniels, A.U., et al., "Evaluation of Absorbable poly(ortho esters) for Use in Surgical Implants," Journal of Applied Biomaterials 5(1):51-64, Spring 1994.

de Haart, M., et al., "Optimization of Chondrocyte Expansion in Culture Effect of TGF beta-2, bFGF and L-Ascorbic Acid on Bovine Articular Chondrocytes," Acta Orthopaedica Scandinavica 70(1):55-61, Feb. 1999.

Dellatore, S.M., et al., "Mimicking Stem Cell Niches to Increase Stem Cell Expansion," Current Opinion in Biotechnology 19(5):534-540, Oct. 2008.

Desoize, B., and J.-C. Ardillier, "Multicellular Resistance: A Paradigm for Clinical Resistance?" Critical Reviews in Oncology/Hematology 36(2-3):193-207, Nov. 2000.

Dillon, G.P., "The Influence of Physical Structure and Charge on Neurite Extension in a 3D Hydrogel Scaffold," Journal of Biomaterials Science. Polymer Edition 9(10):1049-1069, 1998.

dit Faute, M.A., et al., "Distinctive Alterations of Invasiveness, Drug Resistance and Cell-Cell Organization in 3D-Cultures of MCF-7, a Human Breast Cancer Cell Line, and Its Multidrug Resistant Variant," Clinical & Experimental Metastasis 19(2):161-168, 2002.

Dormeyer, W., et al., "Plasma Membrane Proteomics of Human Embryonic Stem Cells and Human Embryonal Carcinoma Cells," Journal of Proteome Research 7(7):2936-2951, Jul. 2008.

(56) References Cited

OTHER PUBLICATIONS

Dornish, M., et al., "Standards and Guidelines for Biopolymers in Tissue-Engineered Medical Products: ASTM Alginate and Chitosan Standard Guides," Annals of the New York Academy of Sciences 944:388-397, Nov. 2001.

Du, C., et al., "Formation of Calcium Phosphate/Collagen Composites Through Mineralization of Collagen Matrix," Journal of Biomedical Materials Research 50(4):518-527, Jun. 2000.

Fan, X., et al., "NOTCH Pathway Blockade Depletes CD133-Positive Glioblastoma Cells and Inhibits Growth of Tumor Neurospheres and Xenografts," Stem Cells 28(1):5-16, Jan. 2010.

Ferrara, N., et al., "Heterozygous Embryonic Lethality Induced by Targeted Inactivation of the VEGF Gene," Nature 380(6573):439-442, Apr. 1996.

Fischbach, C., et al., "Engineering Tumors With 3D Scaffolds," Nature: Methods 4(10):855-860, Oct. 2007.

Florczyk, S.J., et al., "3D Porous Chitosan-Alginate Scaffolds: A New Matrix for Studying Prostate Cancer Cell-Lymphocyte Interactions In Vitro," Advanced Healthcare Materials 1(5):590-599, Sep. 2012.

Florczyk, S.J., et al., "Influence of Processing Parameters on Pore Structure of 3D Porous Chitosan-Alginate Polyelectrolyte Complex Scaffolds," Journal of Biomedical Materials Research Part A 98A(4):614-620, Sep. 2011.

Freed, L.E., et al., "Neocartilage Formation In Vitro and In Vivo Using Cells Cultured on Synthetic Biodegradable Polymers," Journal of Biomedical Materials Research 27(1):11-23, Jan. 1993.

Freed, W.J., et al., "Gene Expression Profile of Neuronal Progenitor Cells Derived From hESCs: Activation of Chromosome 11p15.5 and Comparison to Human Dopaminergio Neurons," PLoS ONE 3(1):e1422, pp. 1-12, Jan. 2008.

Frese, K.K., and D.A. Tuveson, "Maximizing Mouse Cancer Models," Nat Rev Cancer 7:645-658, 2007.

Gåserød, O., et al., "Microcapsules of Alginate-Chitosan. II. A Study of Capsule Stability and Permeability," Biomaterials 20(8):773-783, Apr. 1999.

Glowacki, J., "Engineered Cartilage, Bone, Joints, and Menisci. Potential for Temporomandibular Joint Reconstruction," Cells, Tissues, Organs 169(3):302-308, 2001.

\* cited by examiner

CHITOSAN-ALGINATE SCAFFOLD CELL CULTURE SYSTEM AND RELATED METHODS

CROSS-REFERENCE TO RELATED APPLICATION

This application claims the benefit of U.S. patent application Ser. No. 61/478,429, filed Apr. 22, 2011, expressly incorporated herein by reference in its entirety.

STATEMENT OF GOVERNMENT LICENSE RIGHTS

This invention was made with Government support under EEC9529161 awarded by the National Science Foundation, and under R01EB006043, R01CA134213, and T32CA138312 awarded by the National Institutes of Health. The Government has certain rights in the invention.

BACKGROUND OF THE INVENTION

In vitro studies are an essential component of the initial screening for any anti-cancer therapy, allowing for high-throughput, cost-efficient exploration of potential therapeutics. However, traditional in vitro cell culture on two-dimensional (2D) tissue culture substrates fails to simulate the structure of the tumor microenvironment (TME) present in vivo (i.e., complex cell-cell organization and extracellular matrix (ECM)-cell interactions, which have significant effects on cell phenotype and malignancy). Cells in 2D culture are forced to adhere to a rigid surface and are geometrically constrained, adopting a flat morphology which alters the cytoskeleton regulation that is important in intracellular signaling, and consequently can affect cell growth, migration, and apoptosis. Moreover, organization of the ECM, which is essential to cell differentiation, proliferation, and gene expression, is absent in 2D cultured tumor cell models. These limitations of 2D cultures often result in biological responses to drugs and potentially curative treatments in vitro strikingly different from what is observed in vivo. The ideal in vitro TME model should provide a platform for in vitro drug screening that will better translate to in vivo testing by mimicking both the spatial arrangement of cells and ECM signaling found in tumors in vivo, resulting in the expression of the native in vivo phenotype in these cells.

Often in vitro results often do not translate well to in vivo systems. As a result, costly in vivo animal models remain the most sophisticated and faithful models of the disease. The development of anticancer drugs has been hindered by the lack of effective tumor models that closely mimic the human disease.

Three-dimensional (3D) culture systems are designed to bridge the gap between in vitro and in vivo cancer models. These 3D systems are intended to increase cancer cell malignancy and retain the in vivo phenotype by mimicking the structure of the tumor microenvironment. Natural extracellular matrix materials such as collagen, fibrin, and the commercially available Matrigel matrix (BD Biosciences) have been used, but these animal-source products are expensive, and can potentially transmit pathogens. Synthetic polymers such as poly(lactide-co-glycolide) (PLGA) have also been studied, but they can release acidic degradation products that are toxic to cells, and negatively affect experimental results.

A need exists for improved in vitro models of human cancer that will allow researchers to reduce in vivo experiments by in vitro pre-testing that will defray costs, shorten experimental time, provide a much more controllable environment, and reduce loss of animal life. The present invention seeks to fulfill this need and provides further related advantages.

SUMMARY OF THE INVENTION

The present invention provides methods for culturing cancer cells in vitro using a three-dimensional scaffold, scaffolds that include cultured cancer cells, and methods for using the cultured cancer cells and the scaffolds that include cultured cancer cells in anticancer therapeutic drug development.

In one aspect, the invention provides a method for culturing cancer cells in vitro. In the method, a porous chitosan-alginate scaffold is seeded with cancer cells to provide a scaffold comprising cancer cells and then the seeded cancer cells are cultured in the scaffold for a time sufficient to provide a scaffold comprising cultured cancer cells. In one embodiment, the cultured cancer cells comprise tumor spheroids.

In another aspect of the invention, a scaffold comprising cultured cancer cells is provided.

In one embodiment, the scaffold is a three-dimensional scaffold, comprising a porous chitosan-alginate scaffold and cultured cancer cells.

In one embodiment, the scaffold is produced by the method of the invention.

In certain of the above embodiments, the cultured cancer cells comprise tumor spheroids.

In another embodiment, the invention provides an in vitro cancerous tumor model. In the model, cancerous tumor spheroids are contained in a three-dimensional scaffold comprising chitosan and alginate.

In certain embodiments, cultured cells produced by the methods of the invention and provided in the chitosan-alginate scaffolds of the invention have increased tumor malignancy compared to two-dimensionally cultured cancer cells, increased expression of growth factors compared to two-dimensionally cultured cancer cells, increased expression of the enzyme MMP-2 compared to two-dimensionally cultured cancer cells, increased expression of the extracellular matrix proteins compared to two-dimensionally cultured cancer cells, increased tumorigenicity in vivo compared to two-dimensionally cultured cancer cells, and/or increased $CD31^+$ cell recruitment in vivo compared to two-dimensionally cultured cancer cells.

In a further aspect, the invention provides a method for producing a cancerous tumor in a subject. In the method, cultured cells obtained from the method of the invention for culturing cancer cells or cultured cells from a scaffold of the invention that includes cultured cancer cells are implanted in the subject. In one embodiment, implanting cultured cells comprises implanting a scaffold of the invention comprising cultured cancer cells.

In another aspect of the invention, a method for screening a candidate chemotherapeutic agent in vitro is provided. In the method, cultured cells obtained from the method of the invention for culturing cancer cells are contacted with a candidate chemotherapeutic agent. In one embodiment, contacting cultured cells obtained from the method of the invention for culturing cancer cells comprises contacting the candidate chemotherapeutic agent with the scaffold of the invention comprising cultured cancer cells. In certain embodiments, the method further comprises measuring cell proliferation inhibition, measuring the cell viability, and/or measuring protein expression levels.

In further aspect of the invention, a method for screening a candidate chemotherapeutic agent in vivo is provided. In the method, cultured cells obtained from the method of the invention for culturing cancer cells are implanted in a subject and a candidate chemotherapeutic agent is administered to the subject. In one embodiment, implanting cultured cells obtained from the method of the invention for culturing cancer cells comprises implanting the scaffold of the invention comprising cultured cancer cells. In the method, administering the candidate chemotherapeutic drug comprises administering the drug after a pre-determined period of time. In certain embodiments, the method further comprises comparing the tumor mass or volume measured prior to drug administration and after a pre-determined period of time after drug administration and/or harvesting the tumor mass after a pre-determined period of time after drug administration and analyzing the tumor.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

(15A) PLC and (15B) HepG2 cells were cultured on 2D tissue culture plates, Matrigel matrices, and CA scaffolds, respectively, for 10 days before treatment with doxorubicin. Cell viability relative to untreated cells was determined by the Alamar Blue assay at 24 h, 48 h and 72 h after doxorubicin treatment. $LD_{50}$ was calculated based on viability data. Results are mean±s.d., and * indicates at least one of the group means is statistically different from the others at that time point, p<0.05, n=4.

Figures 16A, 16B, 16C:
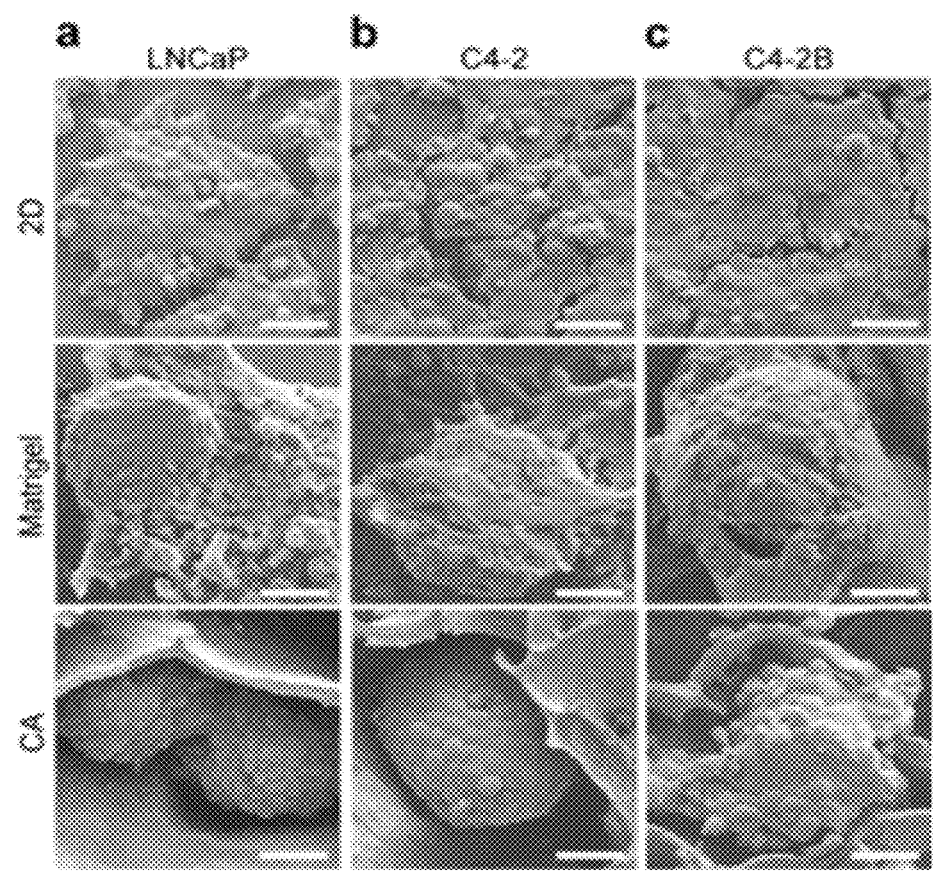

FIGS. 16A-16C compare the morphology of (16A) LNCaP, (16B) C4-2, and (16C) C4-2B human prostate cancer cells were grown on 2D culture plates, Matrigel matrices, and CA scaffolds, respectively, for 15 days before analysis. Scale bars are 40 μm.

DETAILED DESCRIPTION OF THE INVENTION

The present invention provides methods for culturing cancer cells in vitro using a three-dimensional scaffold, scaffolds that include cultured cancer cells, and methods for using the cultured cancer cells and the scaffolds that include cultured cancer cells in anticancer therapeutic drug development.

As noted above, tumor cells cultured on standard two dimension (2D) tissue culture flasks are exposed to a dramatically altered structural microenvironment as compared to in vivo tumors, and thus display altered cell function and response to drug treatment. The present invention provides an in vitro model that can more closely mimic the structure of the tumor microenvironment (TME) and that can dramatically improve the translation of novel chemotherapeutics from in vitro to in vivo testing.

In one aspect, the invention provides a method for three-dimensional cell culture in vitro. In one embodiment, the method includes seeding a porous chitosan-alginate scaffold with cancer cells to provide a scaffold comprising cancer cells; and culturing the cancer cells in the scaffold for a time sufficient to provide a scaffold comprising cultured cancer cells.

In one embodiment, cultured cancer cells form into aggregates known as tumor spheroids. Thus, in one embodiment, a method for producing tumor spheroids in vitro is provided. In the method, a porous chitosan-alginate scaffold is seeded with cancer cells to provide a scaffold comprising cancer cells; and the cancer cells seeded in the scaffold are cultured for a time and under conditions sufficient to provide tumor spheroids in the scaffold.

As used herein, the term "tumor spheroids" refers to spherical, heterogeneous aggregates of proliferating, quiescent, and necrotic cells in culture that retain three-dimensional architecture and tissue-specific functions. Tumor spheroids represent an in vitro model for studies of the biology of both normal and malignant cells.

Figures 2A, 2B, 2C:
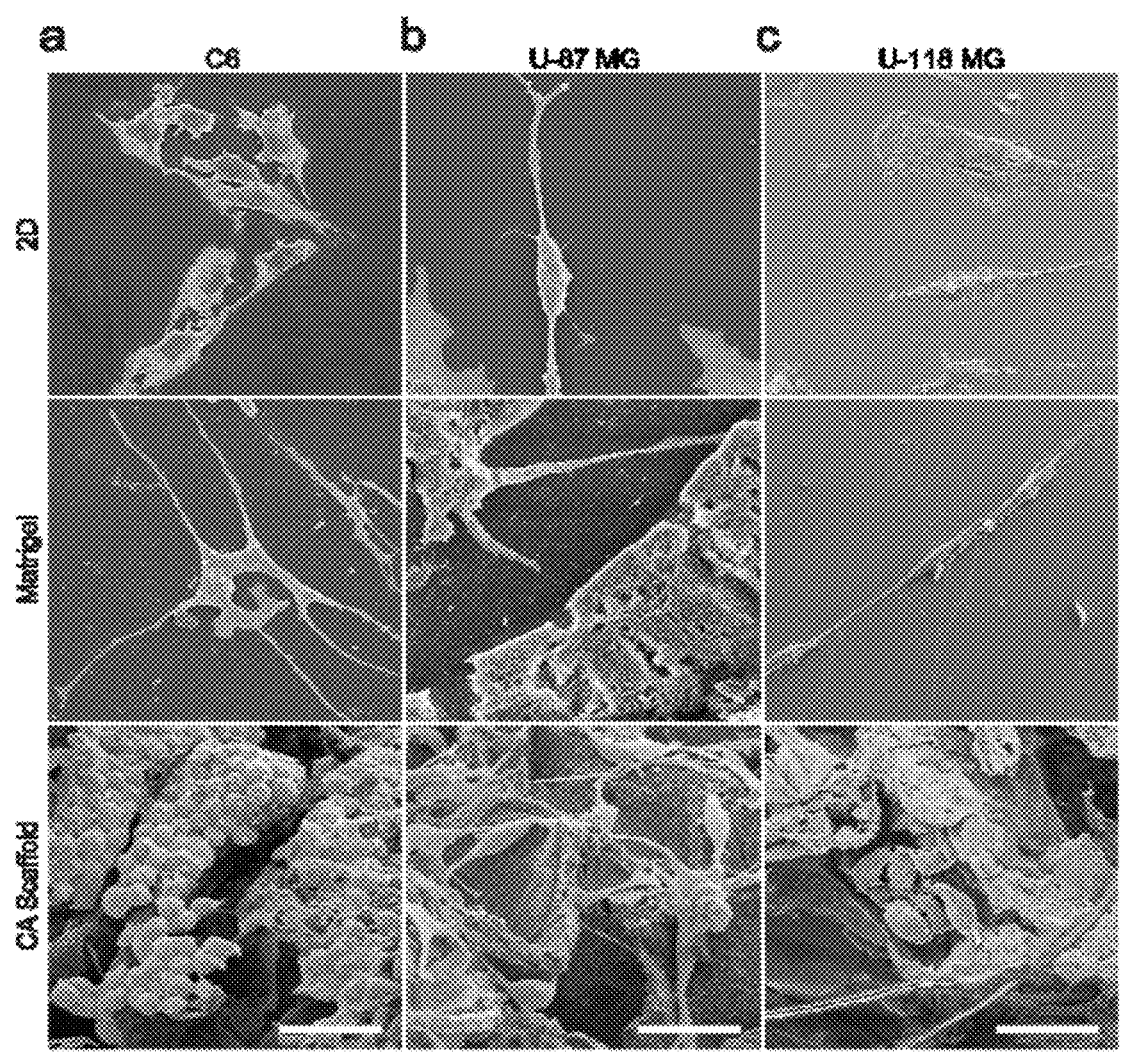
FIGS. 2A-2C compare the morphology of (2A) C6, (2B) U-87 MG, and (2C) U-118 MG glioma cells grown on 2D culture plates, Matrigel matrix, and CA scaffolds, respectively, visualized by SEM imaging. The background is colored for enhanced contrast and the scale bar corresponds to 40 µm.
Figure 9A:
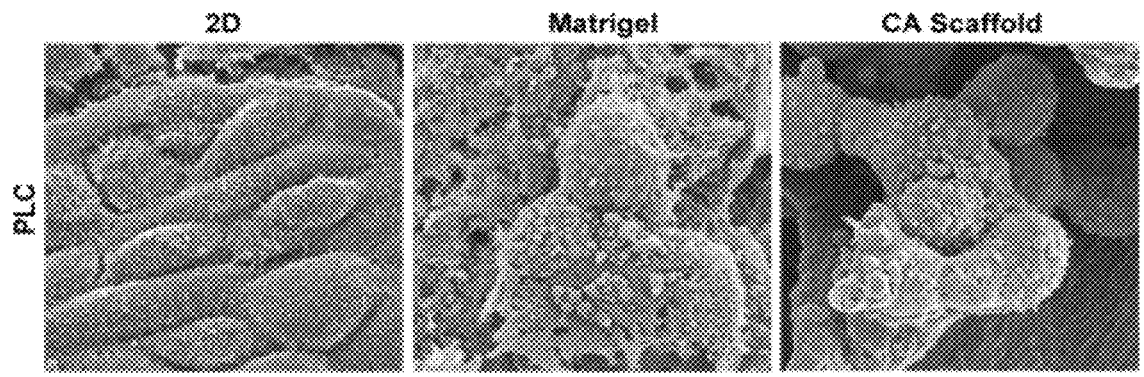
FIGS. 9A and 9B compare images showing the effect of culture conditions on hepatocellular carcinoma cell morphology as observed by SEM. PLC (9A) and HepG2 (9B) cells were cultured on 2D tissue culture plates, Matrigel matrices, and CA scaffolds, respectively, for 10 days. The scale bar represents 10 µm.
Figure 9B:
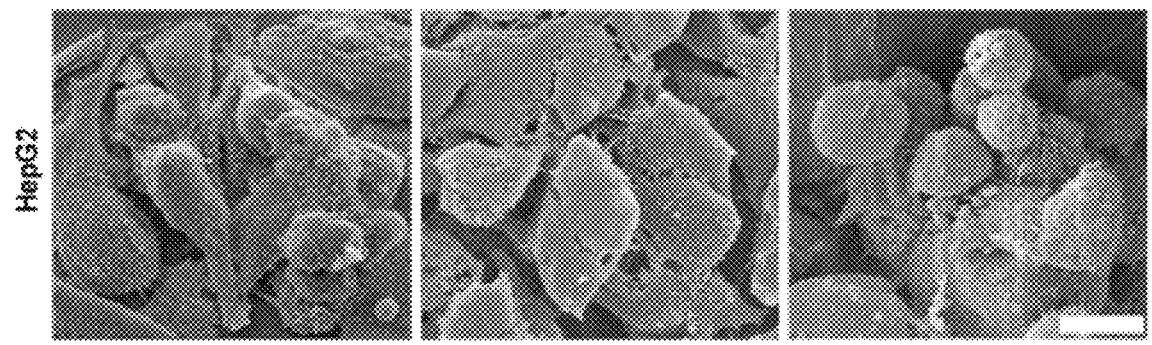

Representative tumor spheroids produced in chitosan-alginate scaffolds by the methods of the invention are illustrated in FIGS. 2A-2C (from C6, U-87 MG, and U-118 MG gliomas cell lines, respectively), FIGS. 9A and 9B (PLC and HepG2 hepatocarcinoma cell lines, respectively), and FIGS. 16A-16C (LNCaP, C4-2, and C4-2B human prostate cancer cell lines, respectively).

As described in detail below, in certain embodiments, the cultured cancer cells (e.g., tumor spheroids) produced in chitosan-alginate scaffolds by the methods of the invention have increased tumor malignancy compared to two-dimensionally cultured cancer cells as well as Matrigel cultured cells. The cultured cancer cells having increased tumor malignancy are cancer cells that do not ordinarily show such malignancy in 2D culture, C6 cells show no increased malignancy because they are predisposed to being highly malignant. C6 cells cultured in the chitosan-alginate scaffold show the unique cell mass (tumor spheroids) like other less malignant cancer cells. Although the generation of the tumor spheroid increases malignancy, the unique matrix/growth environment provided by the chitosan-alginate scaffold further contributes to malignancy. For example, hepatocarcinoma cells cultured in accordance with the method of the invention, GPC, a biomarker for malignant transformation for these cells, is upregulated.

In certain embodiments, the cultured cancer cells (e.g., tumor spheroids) produced in chitosan-alginate scaffolds by the methods of the invention have increased expression of growth factors (e.g., pro-angiogenic growth factors such as VEGF, bFGF, and IL-8) compared to two-dimensionally cultured cancer cells as well as Matrigel cultured cells.

In certain embodiments, the cultured cancer cells (e.g., tumor spheroids) produced in chitosan-alginate scaffolds by the methods of the invention have increased expression of the enzyme MMP-2 compared to two-dimensionally cultured cancer cells as well as Matrigel cultured cells.

In certain embodiments, the cultured cancer cells (e.g., tumor spheroids) produced in chitosan-alginate scaffolds by the methods of the invention have increased expression of the extracellular matrix proteins (e.g., fibronectin and laminin) compared to two-dimensionally cultured cancer cells as well a Matrigel cultured cells.

In certain embodiments, the cultured cancer cells (e.g., tumor spheroids) produced in chitosan-alginate scaffolds by the methods of the invention have increased tumorigenicity in vivo compared to two-dimensionally cultured cancer cells as well as Matrigel cultured cells.

In certain embodiments, the cultured cancer cells (e.g., tumor spheroids) produced in chitosan-alginate scaffolds by the methods of the invention have increased $CD31^+$ cell recruitment (i.e., angiogenesis ability) in vivo compared to two-dimensionally cultured cancer cells as well as Matrigel cultured cells.

In the methods of the invention, culture of cancer cells in the scaffolds does not require any conditions beyond standard tissue culture conditions. In general, tumor spheroids typically form between 3 and 15 days of culture on the scaffolds.

In another aspect, the invention provides an in vitro cancerous tumor model, comprising a cancer cells (e.g., tumor spheroids) cultured in a three-dimensional (3D) scaffold comprising chitosan and alginate.

In a related aspect of the invention, scaffolds comprising cultured cells are provided. In one embodiment, the invention provides a three-dimensional scaffold comprising a porous chitosan-alginate scaffold and cultured cancer cells (e.g., tumor spheroids). In another embodiment, the scaffold comprising cultured cancer cells is produced by the method of the invention.

The scaffolds useful in the compositions and methods of the invention advantageously support cancer cell proliferation and cancerous tumor formation. These scaffolds are porous scaffolds that include a chitosan and an alginate. In these scaffolds, the chitosan is ionically linked to the alginate. In certain embodiments, the scaffolds are further crosslinked by divalent metal atoms. The porous scaffolds useful in the compositions and methods of the invention that include chitosan and alginate are referred to herein as "chitosan-alginate" scaffolds or "CA" scaffolds.

Chitosan and alginate are biocompatible, non-mammalian sourced natural polymers with properties ideal for cell culture scaffold formation. The chitosan and alginate can be used to create a 3D interconnected, CA complex porous structure.

Chitosans, natural polysaccharides derived from the partial deacetylation of chitin, shares structural similarities to glycosaminoglycans present in the native ECM. Chitosans are linear polysaccharides composed of randomly distributed β-(1-4)-linked D-glucosamine (deacetylated unit) and N-acetyl-D-glucosamine (acetylated unit). Chitosans useful for making the scaffolds have an average molecular weight from about 10 kDa to about 1000 kDa. Generally, scaffolds made from higher molecular weight chitosans have greater mechanical strength than scaffolds made from lower molecular weight chitosans. An exemplary range of percentage deacetylation of chitosan useful for making the scaffolds is from about 80% to about 100% deacetylation. Alginates are a family of polyanionic copolymers derived from brown sea algae. Alginates are linear, 1,4-linked polysaccharides of β-D-mannuronic acid and α-L-guluronic acid. In these scaffolds, chitosan is ionically linked to alginate. As used herein, the term "ionically linked" refers to a non-covalent chemical bond or associative interaction between two ions having opposite charges (e.g., electrostatic association between a chitosan amine group and an alginate carboxylic acid group present on alginate).

The scaffolds comprising chitosan and alginate may be crosslinked to increase their mechanical strength. In one embodiment, the porous chitosan/alginate scaffold is crosslinked with divalent metal ions. Thus, in one embodiment, in addition to the ionic linkages between chitosan and alginate, the scaffolds include ionic linkages formed between alginate carboxylic acid groups and divalent metal ions (e.g., $Ca^{2+}$, $Ba^{2+}$, $Mg^{2+}$, $Sr^{2+}$). While not wishing to be bound by theory, it is believed that the divalent metal cations form ionic linkages between adjacent alginate chains, thereby ionically crosslinking adjacent alginate molecules.

In one embodiment, the scaffold further comprises one or more growth factors or inhibitory factors effective for cancer cell proliferation and cancerous tumor formations.

Suitable scaffolds have a porosity of from about 85 to about 96 percent. In one embodiment, the scaffold has a porosity of from about 91 to about 95 percent. In another embodiment, the scaffold has a porosity of from about 94 to about 96 percent.

Suitable scaffolds have an average pore size diameter of from about 50 to about 200 μm. In one embodiment, the scaffold has an average pore size diameter of from about 40 to about 90 μm. In another embodiment, the scaffold has an average pore size diameter of from about 60 to about 150 μm. In one embodiment, the scaffold has a porosity of from about 85 to about 96 percent and an average pore size diameter of from about 50 to about 200 μm.

The porous scaffold possesses mechanical strength. The scaffold has a compressive yield strength of at least 0.35 MPa. In one embodiment, the scaffold has a compressive yield strength of from about 0.35 MPa to about 0.5 MPa. The scaffold has a compressive modulus of from about 5 MPa to 8 MPa. In one embodiment, the scaffold has a compressive yield strength of from about 0.35 MPa to about 0.5 MPa and a compressive modulus of from about 5 MPa to 8 MPa.

In one embodiment, the scaffold has a porosity of from about 85 to about 96 percent, an average pore size diameter of from about 50 to about 200 μm, a compressive yield strength of from about 0.35 MPa to about 0.5 MPa, and a compressive modulus of from about 5 MPa to 8 MPa.

In one embodiment, the scaffold useful in the invention is a porous structure comprising a chitosan, an alginate, and divalent metal cations, wherein the chitosan is ionically linked to the alginate; and wherein the alginate is further crosslinked with divalent metal cations. In one embodiment, the ratio of the chitosan to the alginate is from 1:1 to 4:1.

The preparation of suitable chitosan/alginate scaffolds useful in the methods of the invention are described in Li Z., Ramay H. R., Hauch K. D., Xiao D., Zhang M. Chitosan-alginate hybrid scaffolds for bone tissue engineering, Biomaterials 2005, 26:3919-3928; Li Z., Zhang M. Chitosan-alginate as scaffolding material for cartilage tissue engineering, J Biomed Mater Res A 2005, 75:485-493; and U.S. Pat. No. 7,736,669, each expressly incorporated herein by reference in its entirety. The preparation and characteristics of a representative scaffold useful in the methods of the invention are described in Example 1.

In a further aspect, the invention provides a method for producing a cancerous tumor in a subject. In the method, cultured cells (e.g., tumor spheroids) obtained from the method of the invention for producing a scaffold comprising cultured cancer cells are implanted in a subject. Representative subjects include animals such as mice, rats, and dogs.

Cultured cancer cells (e.g., tumor spheroids) can be separated from the scaffold and implanted or the scaffolds comprising cancer cells can be implanted directed. In one embodiment, implanting cultured cells obtained from the method of the invention for producing a scaffold comprising cultured cancer cells, comprises implanting a scaffold comprising cultured cancer cells.

Implant of cultured cancer cells (e.g., tumor spheroids) can be done between 1-45 days (or even longer if cells are still growing) of culture on the scaffolds. Time depends on the cell line and how it responds to culture in the scaffold. Typically, cells are implanted after 10 days of culture.

In another aspect of the invention, methods for screening candidate anticancer therapeutic drugs are provided.

In one embodiment, the invention provides a method for screening a candidate chemotherapeutic agent in vitro, comprising contacting cultured cells obtained from the method of the invention for producing a scaffold comprising cultured cancer cells with a candidate chemotherapeutic agent. In one embodiment of this method, contacting cultured cells with a candidate chemotherapeutic agent comprises contacting the candidate chemotherapeutic agent with the scaffold comprising cultured cancer cells.

In vitro drug screening can be conducted between 3-45 days (or even longer if cells are still growing) of culture on the scaffolds. Typically, cells are cultured for 10 days before in vitro drug screening.

In one embodiment, the method further comprises measuring cell proliferation inhibition. In another embodiment, the method further comprises measuring the cell viability. In a further embodiment, the method further comprises measuring protein expression levels.

In one embodiment, the invention provides a method for screening a candidate chemotherapeutic agent in vivo, comprising implanting in a subject cultured cells obtained from the method of the invention for producing a scaffold comprising cultured cancer cells; and administering a candidate chemotherapeutic agent to the subject. In one embodiment of this method, implanting cultured cells comprises implanting the scaffold comprising cultured cancer cells.

Drugs can be administered before tumor implant (tumor vaccine type studies), within 1-2 weeks of implant (growth inhibition studies), or once the tumor has reached a certain size, typically 100 $mm^3$ after 2-8 weeks (cell kill and growth inhibition studies). administering the drug after a pre-determined period of time.

In one embodiment, the method further comprises comparing the tumor mass or volume measured prior to drug administration and after a pre-determined period of time after drug administration. In another embodiment, the method further comprising harvesting the tumor mass after a pre-determined period of time after drug administration and analyzing the tumor.

As described herein, in the compositions and methods of the invention, a biocompatible chitosan-alginate complex scaffold was used to model the structure of the TME of cancer cells in vitro. The differences in proliferation rate observed between 2D, Matrigel matrix, and CA scaffold culture conditions can be attributed to the diffusion-limitations imposed by 3D culture environments. The TME is inherently heterogeneous, with the cells at the periphery of a tumor mass receiving the most nutrients and oxygen, while the cells closer to the center are typically hypoxic, whereas 2D monolayer cultured cells have no barrier to this exchange. 3D CA scaffolds allow for cell clusters to form en masse, creating 3D multicellular microenvironments that permit additional interactions between cells that cannot be generated by 2D culture. Changes in ECM deposition patterns and the ability to form tight junctions with neighboring cells in the 3D CA scaffold likely facilitate the formation of these cell clusters. This complex arrangement of cells cultured in CA scaffolds resembles that of multicellular spheroid cultures used to model tumor behavior.

Further analysis of differently cultured cancer cells revealed that expression of the angiogenic factors (e.g., IL-8, bFGF, and VEGF) were elevated in CA scaffold cultured cells compared to both 2D and Matrigel cultured cells. This suggests that the cell-cell and cell-ECM interactions created upon culture in CA scaffolds more faithfully mimicked the native TME conditions that regulate angiogenic factor secretion. Also, for cultured HCC cancer cells, GPC-3 expression, which is correlated with poor patient survival, and is a potential prognostic factor, was significantly elevated in CA cultured HepG2 cells. CA scaffolds stimulate the concurrent expression of multiple markers for increased malignancy, consistent with in vivo observations, suggesting that CA scaffolds provide microenvironmental cues that neither 2D nor Matrigel microenvironments simulate faithfully.

The rapid in vivo tumor expansion by the CA scaffold pre-cultured cells may be a result of the rapid establishment of neovasculature because the growth factors vital for the recruitment and maturation of blood vessels were highly expressed in CA tumor models. The increased pro-angiogenic growth factor secretion by CA scaffold pre-cultured cells promptly overcame the initial lack of vascularization within the flank tumor implant providing sufficient nutrients for rapid tumor formation. As described herein, observed blood vessel formation in histological sections revealed that blood vessel morphology and organization varied tremendously based on pre-treatment. Extravascular pockets of bright red erythrocytes associated with poorly formed leaky vasculature, which is indicative of angiogenesis, were visible in Matrigel pre-cultured HepG2. CA scaffold pre-cultured HCC tumors contained large, round, well endothelialized blood vessels without intraluminal bridging, characteristic of VEGF induced tumor vasculature. Compared to Matrigel pre-cultured HepG2 tumors, there were a large number of erythrocytes in the blood vessel and no notable extravascular erythrocytes in CA HCC samples. Blood vessel formation after 4 weeks of in vivo growth correlated well with angiogenic growth factor expression in vitro, suggesting persistent phenotypical changes induced by in vitro cell culture conditions.

The methods of the invention and the scaffolds provided by the methods are effective for culturing cancer cells. The nature of the cancer cell cultured in the compositions and methods of the invention is not critical. Representative cancer cell lines that have been cultured in the chitosan-alginate scaffold and their properties are summarized in Table 1.

TABLE 1

Properties of cancer cell lines cultured in chitosan-alginate scaffolds.

| Cell line | Species | Disease | Property |
|---|---|---|---|
| C6 | Rat | Glioma | Increased tumor spheroid generation |
| U-87 MG | Human | Glioblastoma | Increased tumor spheroid generation, increased VEGF secretion, increased MMP-2 secretion, increased fibronectin secretion, increased laminin secretion, enhanced tumorigenicity, increased resistance to temozolomide |
| U-118 MG | Human | Glioblastoma | Increased tumor spheroid generation, increased VEGF secretion, increased MMP-2 secretion, increased fibronectin secretion, increased laminin secretion, enhanced tumorigenicity |
| HepG2 | Human | Hepatocellular carcinoma | Increased tumor spheroid generation, increased IL-8 secretion, increased bFGF secretion, increased VEGF secretion, increased GPC-3 expression, increased resistance to doxorubicin, enhanced tumorigenicity |
| PLC | Human | Hepatoma | Increased tumor spheroid generation, increased IL-8 secretion, increased bFGF secretion, increased VEGF secretion, increased GPC-3 expression, increased resistance to |

TABLE 1-continued

Properties of cancer cell lines cultured in chitosan-alginate scaffolds.

| Cell line | Species | Disease | Property |
|---|---|---|---|
| LNCaP | Human | Prostate carcinoma | doxorubicin, enhanced tumorigenicity<br>Increased tumor spheroid generation, increased interaction with PBLs |
| C4-2 | Human | Prostate carcinoma (subline generated from LNCaP injected castrated mice) | Increased tumor spheroid generation, increased interaction with PBLs |
| C4-2B | Human | Prostate carcinoma (subline generated from bone metastases in LNCaP injected castrated mice) | Increased tumor spheroid generation, increased interaction with PBLs |
| TRAMP-C2 | Mouse | Prostate adenocarcinoma | Increased tumor spheroid generation |
| SF767 | Human | Glioblastoma | Increased resistance to temozolomide |
| MMC | Mouse | Mammary carcinoma | Increased tumor spheroid generation |

The following is a description of representative cancer cell growth in chitosan-alginate (Calif.) scaffolds in accordance with the method of the invention.

Gliomas

Gliomas are the most common and lethal type of brain cancer, accounting for 80% of brain tumors, with a 2-year survival of 17-43%. Recent advances in the understanding of glioma biology have revealed effective therapeutic targets, translating to improved patient outcomes. Despite these improvements, the development of anticancer drugs has been hindered by the lack of effective tumor models that closely mimic the human disease.

The present invention demonstrates that CA scaffolds can be used to better mimic the tumor microenvironment of glioma in vitro by promoting a more malignant phenotype. These tumors were developed in vitro by seeding U-87 MG and U-118 MG human glioma cells on CA scaffolds. As a comparison, a cancer stem-like cell line (C6 rat glioma), which is known to be highly invasive and tumorigenic, was also tested. Developed tumor malignancy was assessed by ELISA and dot blot analyses of secreted key growth factors and extracellular matrix. Further assessment of in vitro developed U-87 MG tumors was performed by implantation into mice and monitoring tumor growth and blood vessel formation. In vitro tumors from C6 cells were also implanted as a control.

Glioma Cell Incorporation into CA Scaffolds

CA scaffolds are prepared by lyophilizing and crosslinking a physical mixture of chitosan and alginate. The formed scaffolds are highly porous to allow for the influx of cells throughout the scaffold, and provide a large surface area for cell attachment and proliferation, ideal for modeling the tumor microenvironment.

The preparation of a representative chitosan-alginate scaffold and its seeding with cancer cells is described in Example 2.

The tumor model was established by seeding U-87 MG and U-118 MG human glioma cells on the scaffolds and allowing the tumor cells to proliferate in vitro for 10 days. A control tumor model was established using C6 rat glioma cells which have a highly malignant phenotype, and thus should be relatively unresponsive to culture conditions.

Figure 1A:
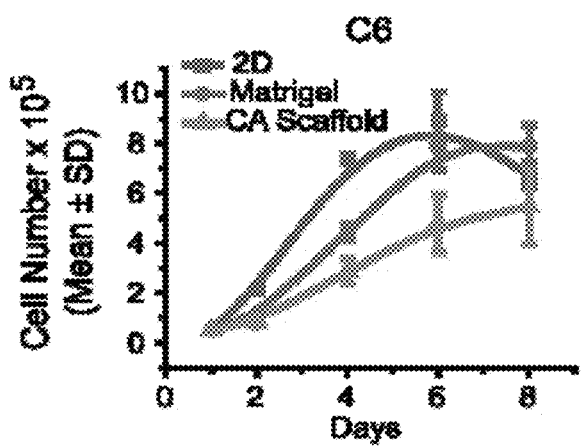
FIGS. 1A-1C compare the ability of chitosan-alginate (Calif.) scaffolds to provide a growth environment for tumor cells in vitro. Proliferation of (1A) C6, (1B) U-87 MG, and (1C) U-118 MG glioma cells cultured on 2D culture 24-well plates, Matrigel matrix, and CA scaffolds, respectively, after 2, 4, 6, 8, and 10 days of cell culture, as determined by the Alamar Blue viability assay.
Figure 1B:
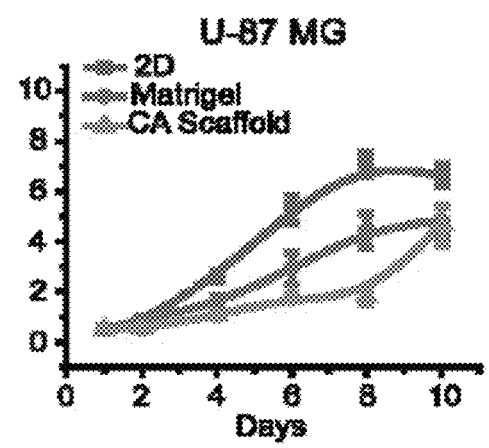
Figure 1C:
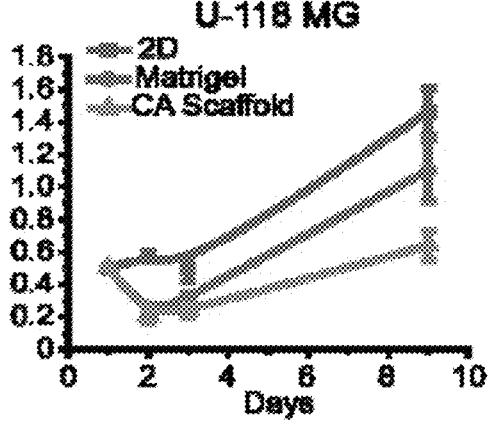

Cell incorporation into CA scaffolds was monitored through proliferation and Scanning Electron Microscopy (SEM) analyses. All cell lines were able to proliferate within the CA scaffolds indicating the biocompatibility of the scaffold. Cells were also grown on standard 2D culture wells (24-well plates) and in 3D Matrigel matrix for comparison. The proliferation of cells grown on CA scaffolds was slightly retarded compared to 2D and Matrigel cultures (FIG. 1). This behavior more closely resembles that of tumors in vivo which grow more slowly than in standard in vitro cell cultures. 2D cultures supply cells with unlimited amounts of nutrients and sufficient oxygen allowing them to grow rapidly, whereas in vivo tumors must recruit blood vessels before they can begin to proliferate rapidly. A slower rate of diffusion of oxygen and nutrients to cells in the interior of the CA scaffolds may account for the retarded growth rate observed, whereas nutrients and oxygen readily diffuse to the interior of the Matrigel gel matrix.

To examine cell morphology, SEM images were acquired of cells grown under the three different conditions (FIG. 2). All three cell lines displayed altered morphologic phenotypes dependent on the culture environment. Cells cultured on 2D wells displayed a linear and elongated morphology, whereas those grown in the 3D culture condition created by the Matrigel matrix developed many invadopodia. Glioma cells cultured on CA scaffolds had a more rounded appearance. Although invadopodia is an indicator of malignancy, this morphology is seen in invading cells rather than glioma cells of solid tumors. Cells in solid tumors exhibit a more rounded and interconnected morphology, similar to that seen in cells grown on CA scaffolds. Therefore, the CA scaffolds are able to provide a growth environment that promotes the formation of solid tumor-like cells.

Differential Growth Factor Expression in Cells Pre-Cultured on CA Scaffolds

Figure 3A:
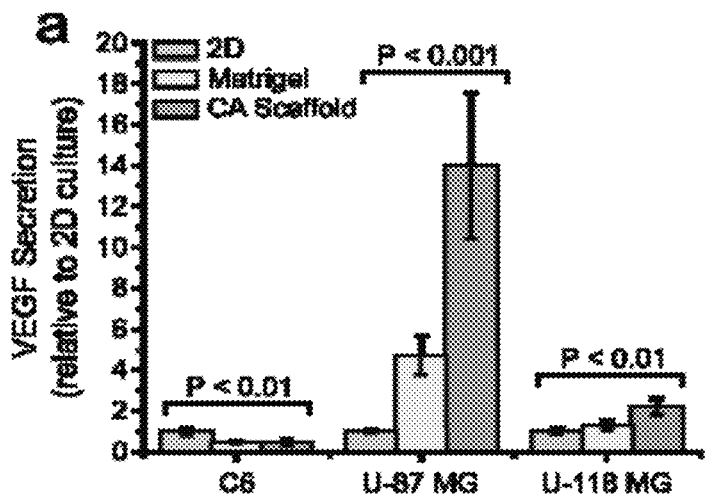
FIGS. 3A-3D compare phenotypic changes in glioma cells based on in vitro pre-culture conditions, assessed by ELISA and dot blot analyses. The secretion of (3A) VEGF and (3B) Matrix metalloproteinase-2 in C6, U-87 MG, and U-118 MG cells pre-cultured on 2D 24-well culture plates, Matrigel matrix, and CA scaffolds, respectively, as determined by ELISA. Fibronectin (3C) and laminin (3D) secretion in cells pre-cultured on the three matrices as determined by dot blot analyses. *, P<0.01; , P<0.001; *, P<0.0001, by student's t-test (N=4).
Figure 3B:
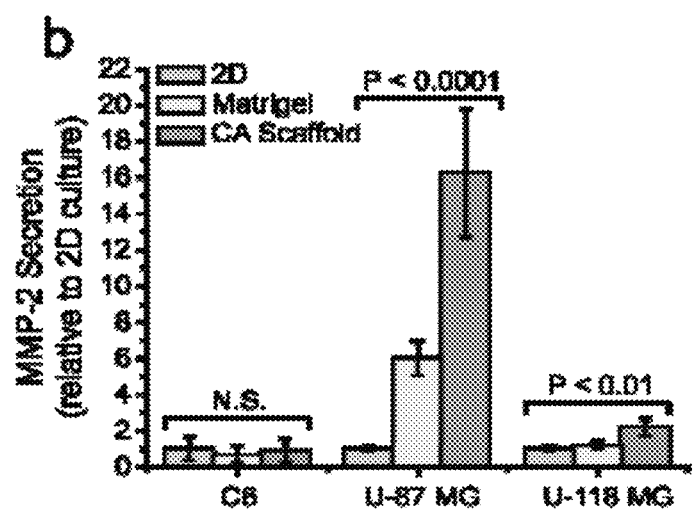
Figure 3C:
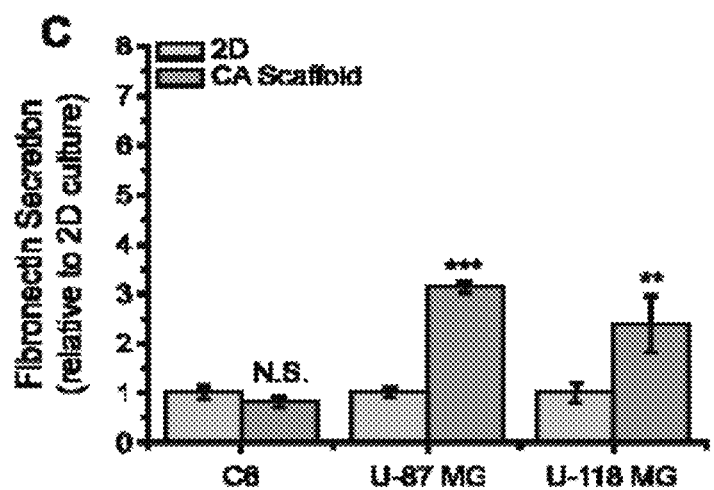
Figure 3D:
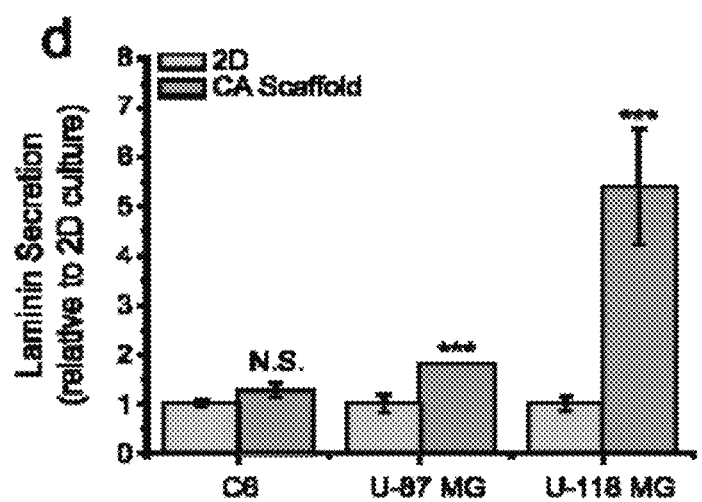

To determine the effect of 3D culture on the malignant potential of glioma cells, we performed ELISA analyses on the secreted growth factor VEGF (FIG. 3A) and the enzyme MMP-2 (FIG. 3B). Additionally, dot blot analyses were performed to quantify the secretion of extracellular matrix (ECM) proteins, laminin (FIG. 3C) and fibronectin (FIG. 3D). These particular growth factors were evaluated as they play a significant role in angiogenesis and various other pathways in glioma which promote growth, invasion, and resistance to chemotherapeutic drugs. Overexpression of these factors contributes to an increase in cancer malignancy.

VEGF secretion plays a pivotal role in blood vessel recruitment to the tumor. As shown in FIG. 3A, VEGF secretion by C6 cells grown in CA scaffolds was $0.47\pm0.16$ fold ($P<0.01$, $N=3$) lower than those grown on 2D culture wells. U-87 MG cells in CA scaffolds, on the other hand, showed a $13.98\pm3.58$ fold ($P<0.001$, $N=3$) higher VEGF secretion than those on 2D culture wells. U-118 MG cells in CA scaffolds also showed an increase in VEGF secretion ($1.91\pm0.50$ fold, $P<0.01$, $N=3$), as compared to 2D cultured cells.

MMP-2 breaks down the extracellular matrix to provide room for cell proliferation and endothelial cell recruitment for angiogenesis. As shown in FIG. 3B, MMP-2 secretion did not change significantly in C6 cells cultured in CA scaffolds, whereas secretion increased $16.24\pm3.58$ fold ($P<0.0001$, $N=3$) in U-87 MG cells and $2.17\pm0.50$ fold ($P<0.01$, $N=3$) in U-118 MG cells cultured in CA scaffolds as compared to 2D cultures.

Fibronectin and laminin equip cells for angiogenesis by providing a signal and structure for endothelial cell attachment and proliferation. Secretion of these extracellular matrix proteins were not significantly changed in C6 cells cultured in CA scaffolds as compared to 2D culture wells, shown in FIGS. 3C and 3D. Fibronectin secretion increased $3.13\pm0.13$ fold ($P<0.0001$, $N=4$), and laminin secretion increased $1.81\pm0.01$ fold ($P<0.0001$, $N=4$) in U-87 MG cells cultured on CA scaffolds as compared to 2D culture wells. For U-118 MG cells cultured on CA scaffolds, fibronectin secretion increased $2.38\pm0.57$ fold ($P<0.001$, $N=4$) and laminin secretion increased $5.39\pm1.19$ fold ($P<0.0001$, $N=4$) as compared to 2D culture wells. Matrigel samples were not tested because they contain both fibronectin and laminin.

From these data it is apparent that CA scaffolds promote the formation of a more malignant phenotype in human glioma cell lines as compared to standard 2D and Matrigel culture conditions. The up-regulation of growth factors observed upon culture in CA scaffolds indicates these cells have an enhanced ability to modify their extracellular space, and are able to create a niche conducive to their progression. This behavior is more representative of the human glioma tumor in vivo because cells in vivo must restructure the extracellular matrix and secrete growth factors to promote angiogenesis. As expected, C6 cells were relatively unresponsive to their environment. This may be due to the fact that this cell line comprises mainly cancer stem cells which favor the expression of factors that promote growth and tumorgenicity, even in standard long-term in vitro growth conditions. The highly malignant phenotype of C6 cells in standard 2D culture conditions were not further increased upon culture in the 3D environment supplied by either Matrigel matrix or CA scaffolds.

Tumorigenesis of Cells Pre-Cultured on CA Scaffolds

Figure 4A:
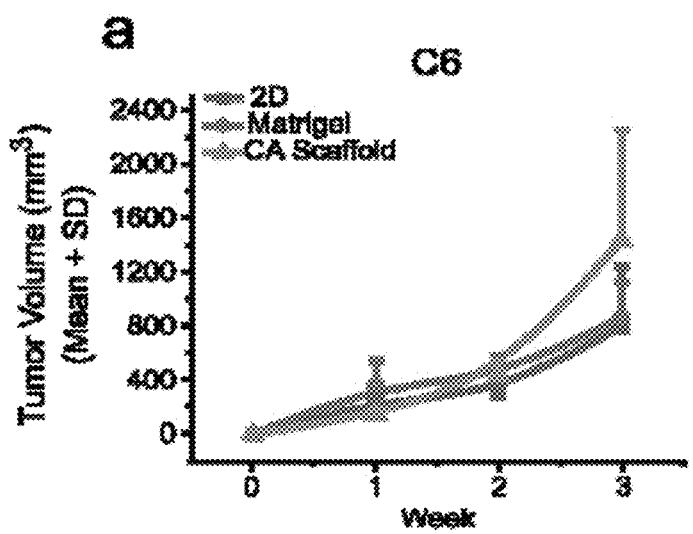
FIGS. 4A and 4B compare in vivo tumorigenesis of glioma cells pre-cultured under various in vitro culture conditions. Growth rates of tumors formed from implants of 2D, Matrigel matrix, and CA scaffold pre-cultured (4A) C6 or (4B) U-87 MG cells as determined by caliper measurements. *, P<0.01; , P<0.001; *, P<0.0001, by one-way ANOVA (N=6).
Figure 4B:
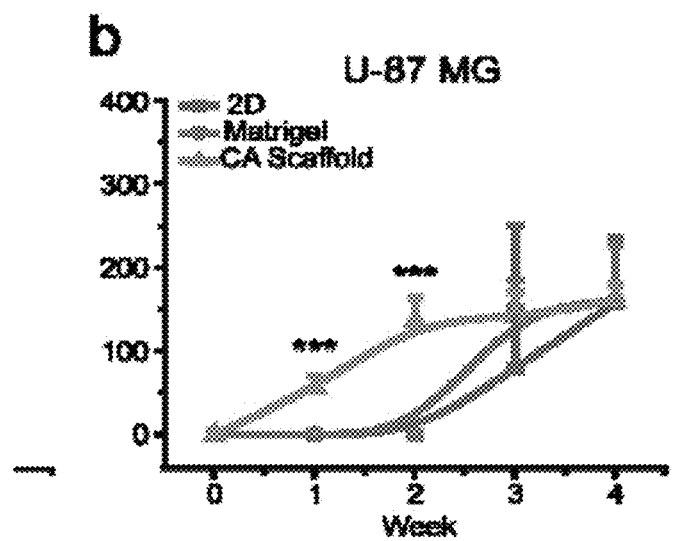

To further assess the malignancy of glioma cells cultured in CA scaffolds as compared to 2D and Matrigel cultures, and to confirm the increase in malignancy was physiologically relevant, the tumorigenicity of U-87 MG cells was determined by implantation of the pre-cultured matrices into nude mice. 2D, Matrigel, and CA scaffold pre-cultured C6 cells were also implanted as a control. As anticipated, C6 cells implanted into mice formed tumors at approximately the same rate regardless of pre-culture condition (FIG. 4A). This is attributable to the minimal difference in growth factor and extracellular matrix secretion in these already highly malignant cells. U-87 MG cells implanted in mice showed a positive correlation between accelerated tumor growth rate and pre-culture in CA scaffolds (FIG. 4B). This increased rate of tumor formation over weeks one ($P<0.0001$, $N=6$) and two ($P<0.0001$, $N=6$) provides further support that the CA scaffolds were able to mimic the tumor microenvironment as U-87 MG cells were able to develop a malignant profile prior to implantation, allowing for rapid tumor development. However, this rapid tumor growth was not sustained; after an initial burst of tumor growth, the implanted CA scaffold pre-cultured tumors began to grow at a similar rate to the 2D and Matrigel pre-cultured tumors.

Figure 5A:
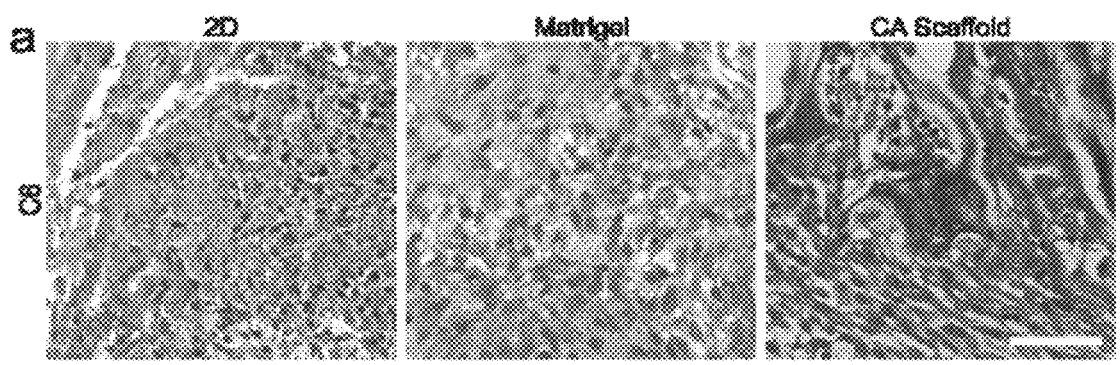
FIGS. 5A and 5B compare histological analyses of glioma tumors grown in athymic nude mice 3 weeks after implantation of pre-cultured glioma cells under various in vitro culture conditions. Masson's trichrome stained histology slides of (5A) C6 and (5B) U-87 MG tumors formed from cells pre-cultured on 2D culture 24-well plates, Matrigel matrix, and CA scaffolds, respectively. Cell nuclei are stained dark red, cytoplasm is stained light red, connective tissue is stained dark blue, and Matrigel is stained light blue. Scale bar corresponds to 50 µm.
Figure 5B:
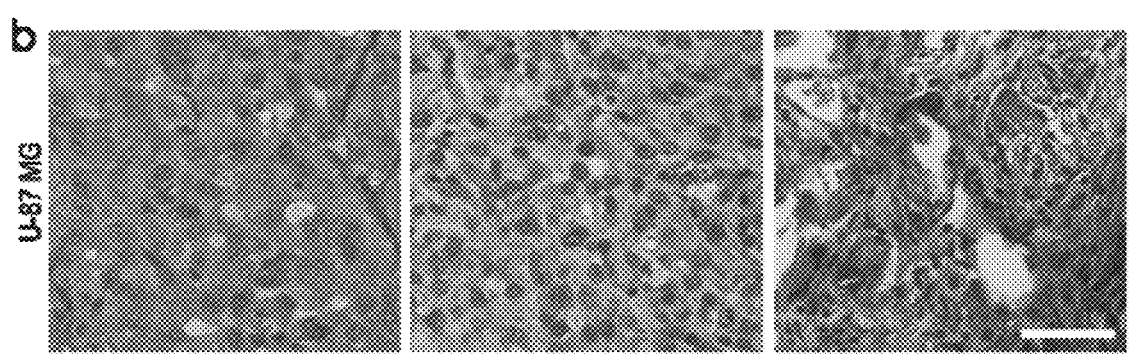

Masson's trichrome histological analysis of C6 tumors after 3 weeks of implantation showed no significant changes in cell morphology or deposition of extracellular matrix regardless of pre-culture condition (FIG. 5A), which agrees with the in vitro findings. Masson's trichrome histological analysis of U-87 MG tumors 4 weeks following implantation showed an enhanced extracellular matrix secretion in tumors formed from CA scaffold pre-cultured cells (FIG. 5B). This increased deposition of the extracellular matrix provides further evidence of higher malignancy in U-87 MG cells cultured in CA scaffolds.

Angiogenesis in Tumors Formed from CA Scaffold Pre-Cultured Cells

Figure 6A:
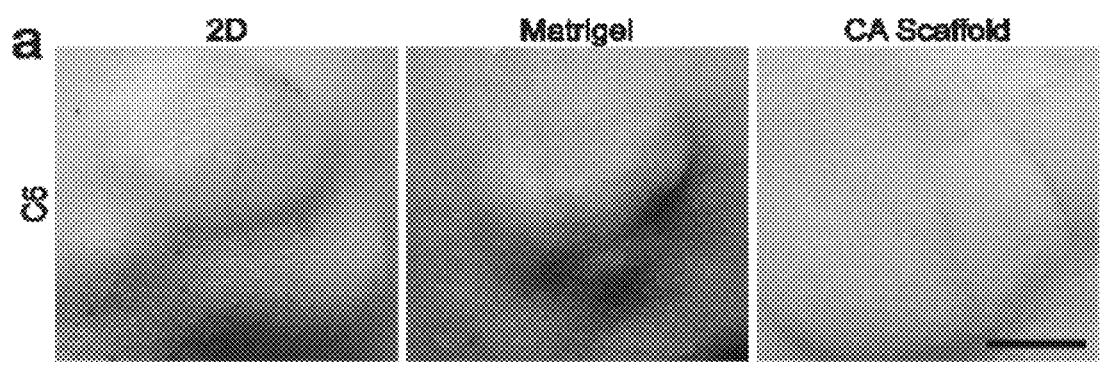
FIGS. 6A and 6B are images comparing angiogenesis around tumors formed from glioma cells pre-cultured on 2D culture 24-well plates, Matrigel matrix, and CA scaffolds, respectively. Vasculature surrounding (6A) C6 and (6B) U-87 MG tumors were photographed in live, anesthetized mice. Scale bars correspond to approximately 5 mm.
Figure 6B:
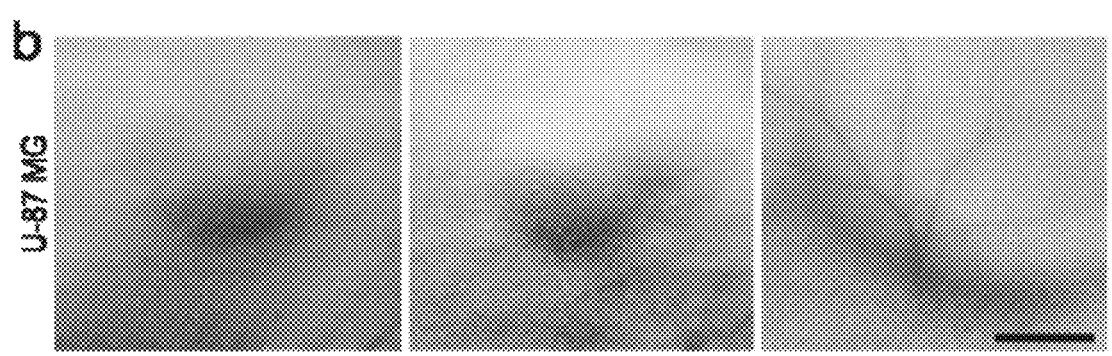
Figure 7A:
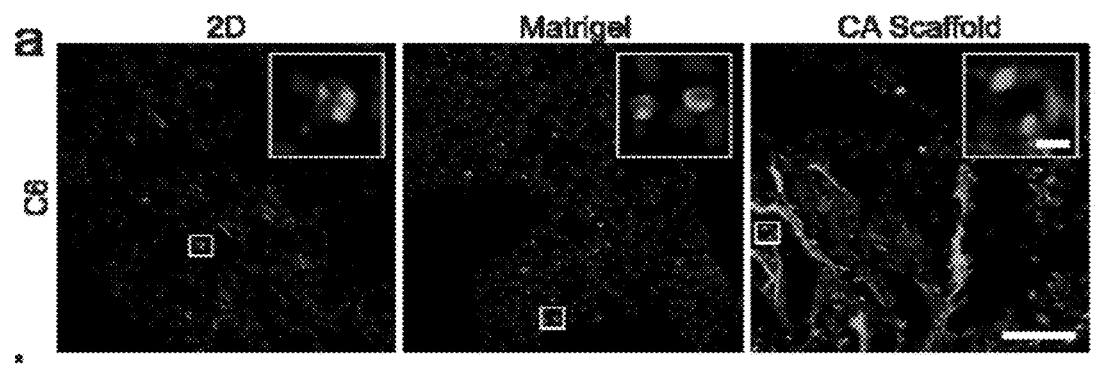
FIGS. 7A and 7B compare immunohistochemistry of tumors grown from glioma cells pre-cultured on 2D culture 24-well plates, Matrigel matrix, and CA scaffolds, respectively. C6 (7A) and U-87 MG (7B) tumor sections were harvested 3 weeks after implantation of the pre-cultured cells, stained with anti-CD31 to visualize blood vessels (green), and counterstained with DAPI (blue) with inlays to provide more details of the blood vessel structure. Scale bars correspond to 100 µm and 10 µm for the main display and inlay, respectively.
Figure 7B:
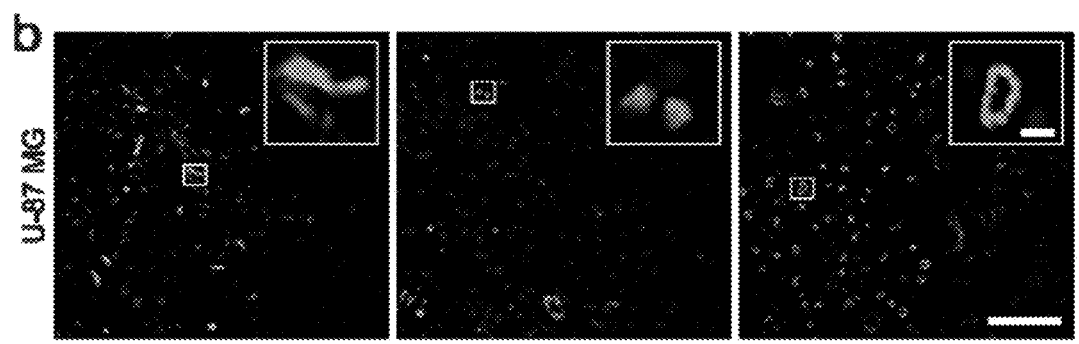

A key hallmark of malignant tumor progression is angiogenesis. Xenograft tumors formed from 2D cultured cells, Matrigel matrix cultured cells, and CA scaffold cultured cells were photographed in live mice to show vasculature (FIG. 6). Visible blood vessel formation in C6 tumors was not affected by pre-culture conditions as expected from the similarity in growth factor expression levels and tumor growth rate (FIG. 6A). Angiogenesis was highly visible in vasculature to U-87 MG tumors from cells pre-cultured in CA scaffolds (FIG. 6B). No blood vessel recruitment was evident around tumors formed from 2D or Matrigel pre-cultured U-87 MG cells. Even if blood vessels are not visible on the tumor surfaces, endothelial cells can still penetrate the tumor for angiogenesis. To visualize the recruitment of endothelial cells and established blood vessels within the tumors, $CD31^+$ cells were visualized using immunohistochemistry (FIG. 7). There was no apparent difference in $CD31^+$ cell recruitment in C6 tumors regardless of pre-culture condition (FIG. 7A). Further, these cells were randomly distributed throughout the tumor and lacked blood vessel structure. On the other hand, U-87 MG tumors formed from CA scaffold pre-cultured cells showed a greatly enhanced recruitment of $CD31^+$ cells indicating an improved ability for angiogenesis (FIG. 7B). This is further corroborated by the numerous circular blood vessel structures visible in these tumors, whereas the tumors formed from 2D and Matrigel matrix pre-cultured U-87 MG cells showed fewer, randomly distributed $CD31^+$ cells. This accelerated rate of structured angiogenesis in tumors formed from CA scaffold pre-cultured U-87 MG cells can be attributed to the increased expression levels of growth factors in these cells, indicating their enhanced malignant potential.

As described above, U-87 MG cells in CA scaffolds exhibited a slower proliferation rate when cultured in vitro (FIG. 1), while CA scaffold cultured U-87 MG cells showed accelerated tumor growth in vivo (FIG. 4B). The proliferation rate in vitro is affected by the cells' ability to acquire the oxygen and nutrients which diffuse more slowly in CA scaffolds than on 2D culture plates and Matrigel, which resulted in a slower proliferation rate in CA scaffolds. The tumor growth rate in vivo is significantly affected by its ability to recruit blood vessels that provide pathways for biofluid exchange. The results shown in FIG. 7B further confirms the correlation between blood vessel formation and tumor growth rate.

CA scaffolds are able to provide a growth environment for glioma cells in vitro which is similar to the tumor microenvironment structure encountered in xenograft tumors in vivo. This reproducible and easily modifiable experimental system offers a number of advantages: they can be easily transferred into mice for rapid xenograft tumor growth, they can be used to pre-screen therapies to reduce the amount of in vivo screening, and they can be easily degraded to harvest single, viable cells for analyses such as PCR and flow cytometry. This will not only reduce the amount of time needed to complete experiments, but also reduce the enormous costs and loss of animal life associated with in vivo models.

Hepatocellular Carcinoma

Hepatocellular carcinoma (HCC) is one of the most common solid malignancies with over a million new cases diagnosed annually worldwide. Most patients with HCC present in an advanced stage are not amenable to potentially curative treatments (e.g., orthotopic liver transplantation and surgical liver resection). Even the most recent advancements in chemotherapeutics (e.g., Sorafenib) prolong survival by merely three month. This result reflects an urgent need for the development of new and more effective therapies.

Unfortunately, experimental models used to test novel HCC therapies are limited. Costly in vivo animal models remain the most sophisticated and faithful models of the disease.

CA scaffolds were used to mimic the structure of the in vivo TME of HCC in vitro by inducing a biological response in the HCC cell lines, PLC/PRF/5 (PLC) and HepG2. This in vitro HCC tumor model more closely resembles the in vivo tumor than traditional 2D cell culture or Matrigel, and can be used as a platform to rapidly evaluate anti-cancer therapies that will translate better to in vivo studies and promote effective treatment of this deadly disease.

In Vitro Cell Response

Figure 8A:
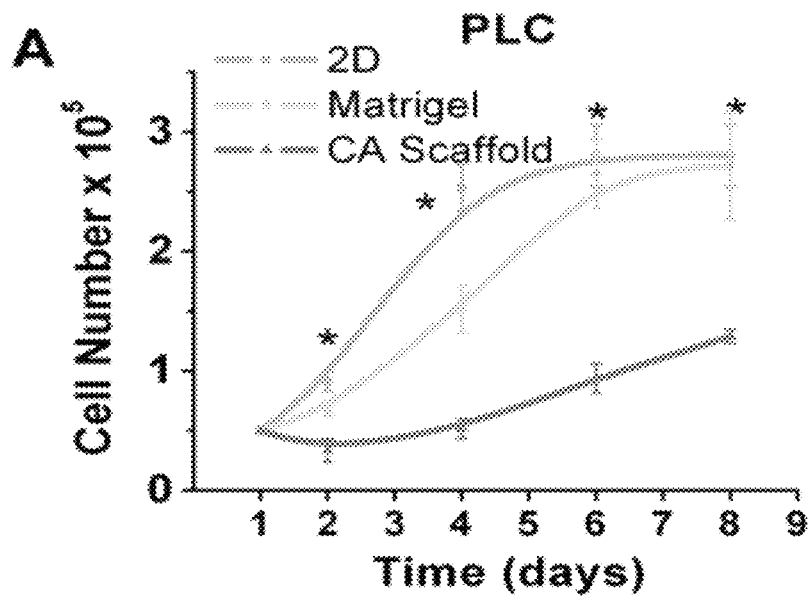
FIGS. 8A and 8B compare the effect of culture conditions on hepatocellular carcinoma cell proliferation. Populations of (8A) PLC and (8B) HepG2 cells cultured for a period of 8 days on 2D plates, Matrigel matrices, and CA scaffolds, respectively. Cellular proliferation was determined by the Alamar Blue assay. Results are shown as mean±s.d., and * indicates at least one of the group means is statistically different from the others at that time point, p<0.05, n=4.
Figure 8B:
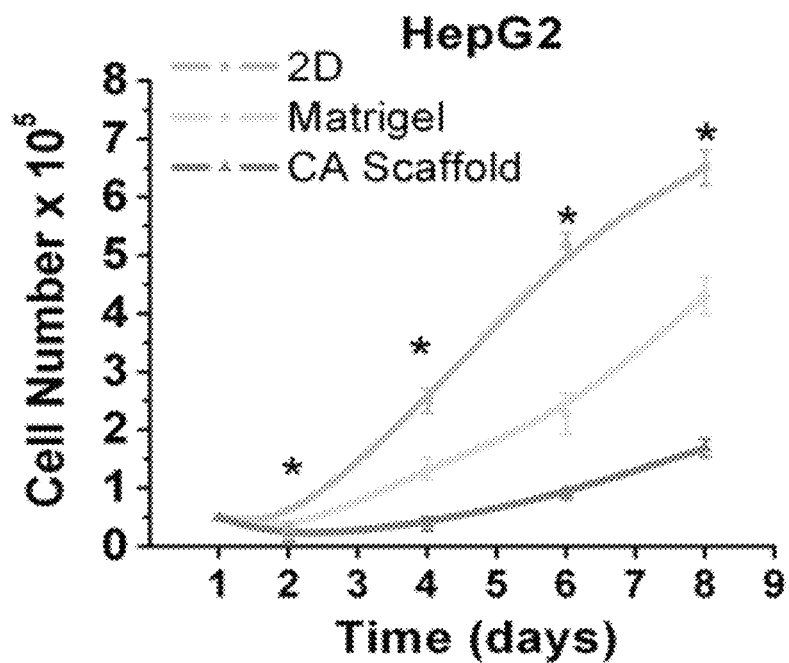

In vitro models of hepatocellular carcinoma (HCC) were generated by culturing human PLC/PRF/5 (PLC) or HepG2 cells in either a 2D surface, Matrigel, or CA scaffold environment. The proliferative response of these cells was compared using the Alamar Blue assay. As shown in FIGS. 8A and 8B, successful expansion and propagation was observed for both PLC and HepG2 cell lines in all three substrate conditions. Statistically significant differences in PLC proliferation were observed at 2 ($p<0.01$), 4 ($p<0.01$), 6 ($p<0.01$) and 8 ($p<0.01$) days. Similarly, HepG2 also exhibited statistically significant changes in proliferation at 2 ($p<0.01$), 4 ($p<0.01$), 6 ($p<0.01$), 8 ($p<0.01$) days. However, the proliferation rates in 3D culture conditions (i.e., Matrigel and CA scaffolds were significantly lower than the rates in the 2D condition).

The effect of the culture microenvironment on cell morphology was evaluated by SEM, which showed significant differences in cell morphology and organization between 2D and 3D culture conditions for both HCC cell lines (FIGS. 9A and 9B). PLC cells cultured on a flat monolayer 2D condition exhibited an elongated morphology, whereas when cultured in Matrigel, cells exhibited an enlarged spherical morphology, and clustered together within the provided ECM. This 3D organization of PLC cells was also observed when cultured in CA scaffolds, where spherical cells formed large dense aggregates within the pores of the scaffold. Similarly, HepG2 cells exhibited a spherical morphology when cultured in either Matrigel or CA scaffolds, and demonstrated greater organization by formation of stacked groupings of cells that filled the scaffold pores.

Cellular Protein Expression

Figure 10A:
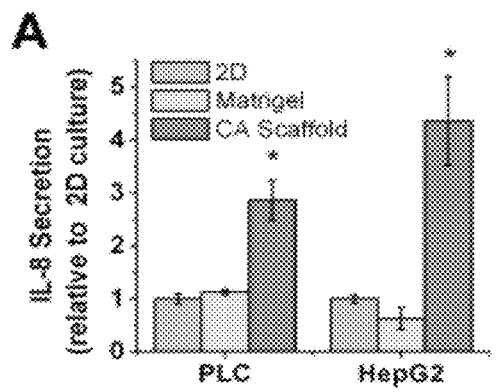
FIGS. 10A-10C compare growth factor expression profiles of hepatocellular carcinoma cells cultured in vitro for 10 days: (10A) IL-8, (10B) bFGF, and (10C) VEGF secretion by PCL and HepG2 cells cultured on 2D tissue culture plates, Matrigel matrices, and CA scaffolds, respectively, as determined by ELISA. Results are mean±s.d., and * indicates at least one of the means in that group is statistically different from the others, p<0.05, n=4.
Figure 10B:
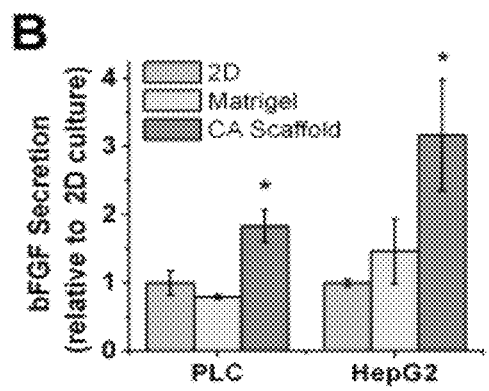
Figure 10C:
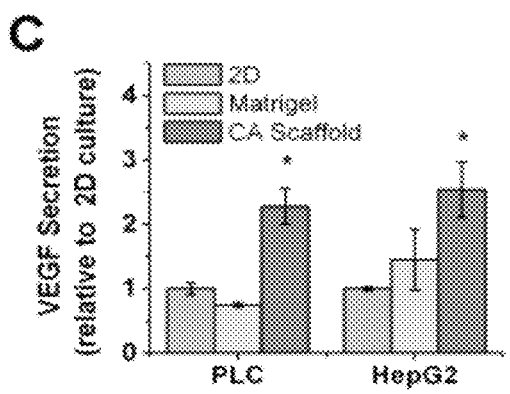

The protein expression profile of the cultured cells was examined to determine if the various culture conditions would affect the secretion of growth factors or cytokines that may stimulate tumor expansion and promote malignancy. The expansion of malignant tumors has been shown to be dependent on the development and maintenance of the surrounding vascular network in vivo, therefore, the expression of pro-angiogenic growth factors IL-8, bFGF, and VEGF, secreted by HCC cells, was evaluated using ELISA assays. IL-8 has been implicated in cell proliferation, invasion, and recruitment of blood vessels for cancer cell survival. As illustrated in FIG. 10A, IL-8 expression was upregulated by both PLC and HepG2 cells cultured in CA scaffolds, by a factor of 2.86±0.38 fold ($p<0.01$) and 4.37±0.84 fold ($p<0.01$), respectively, as compared to 2D cultured cells. bFGF is a chemotactic signal that induces endothelial cell migration, an angiogenic phenotype, stimulating proliferation, and the release of ECM remodeling enzymes. As shown in FIG. 10B, CA scaffold-cultured PLC and HepG2 cells both increased the expression of bFGF by a factor of 1.83±0.22 fold ($p<0.01$) and 3.16±0.81 fold ($p<0.01$), respectively, as compared to their 2D counterparts. VEGF is a multi-functional cytokine that plays an important role in angiogenesis. VEGF expressed by PLC and HepG2 cells cultured in CA scaffolds was significantly higher than that of 2D cultured cells, by a factor of 2.28±0.27 fold ($p<0.01$) and 2.54±0.43 fold ($p<0.01$), respectively (FIG. 10C).

Figure 11:
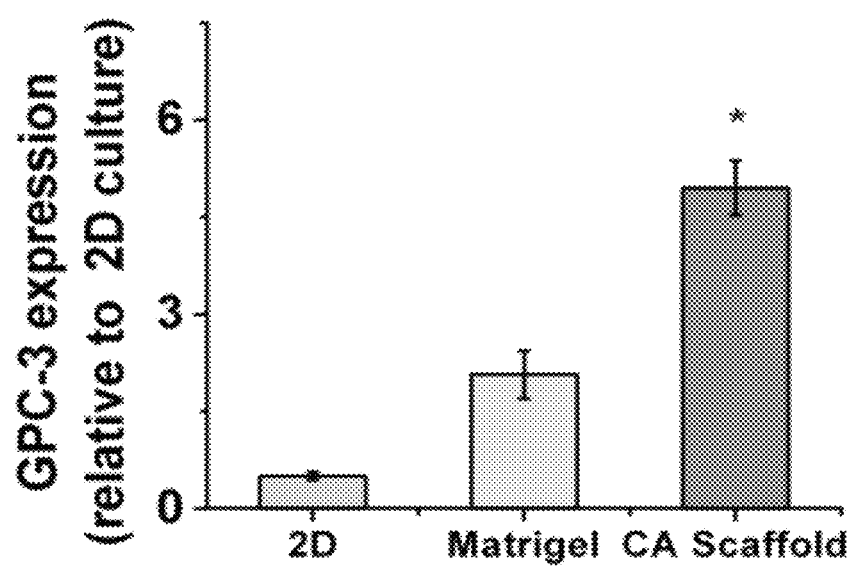
FIG. 11 compares glypican-3 (GPC-3) expression by HepG2 hepatocellular carcinoma cells cultured in vitro for 10 days on 2D tissue culture plates, Matrigel matrices, and CA scaffolds, respectively, as determined by dot blot analysis. Results are mean±s.d., and * indicates at least one of the means is statistically different from the others, p<0.05, n=4.

Glypican-3 (GPC-3) is a surface proteoglycan expressed in up to 83% of HCC's and has been used as a specific marker of a cell's malignant transformation (26-28). HepG2 is known to express a high level of this gene, while PLC does not. Dot blots used to determine the GPC-3 expression level showed that GPC-3 expression in HepG2 cells cultured in 3D Matrigel and CA scaffolds was greatly increased, by 2.6±0.37 fold and 5.5±0.42 fold ($p<0.01$), respectively, compared to 2D culture (FIG. 11).

In Vivo Tissue Response

Figure 12A:
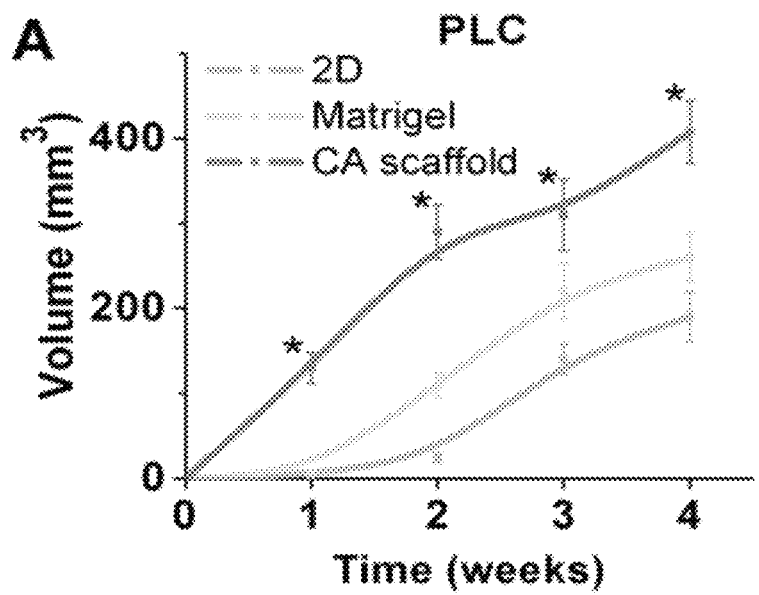
FIGS. 12A and 12B compare the effect of pre-culture conditions on tumor growth in vivo. Tumor volume induced by subcutaneously implanted (12A) PLC and (12B) HepG2 cells pre-cultured on 2D tissue culture plates, Matrigel matrices, and CA scaffolds, respectively, as determined by caliper measurements. Results are mean±s.d. and * indicates at least one of the group means is statistically different from the others at that time point, p<0.05, n=4.
Figure 12B:
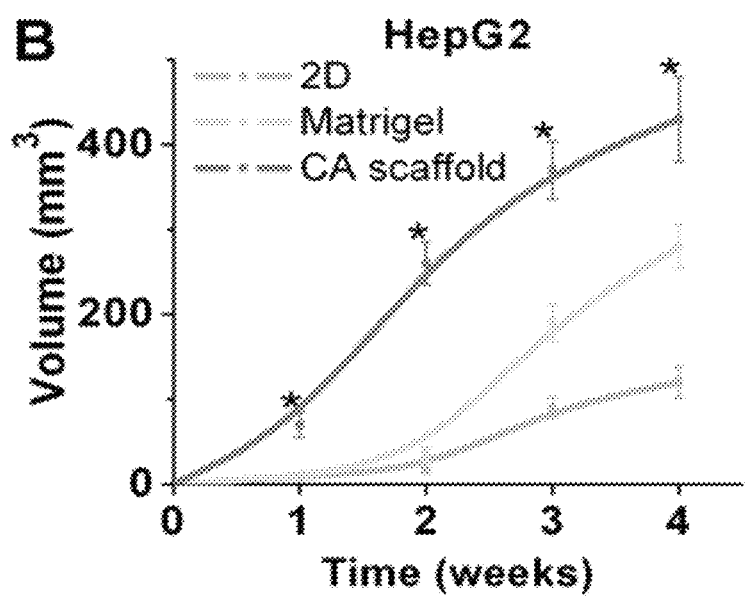

The in vivo tissue response to implantation of HepG2 and PLC cells pre-cultured in the three in vitro conditions (i.e., 2D, Matrigel, and CA scaffold cultures) was evaluated in a subcutaneous xenograft model in athymic nude mice. Initial cell numbers were normalized to the number of cells in CA scaffold culture. Tumor volumetric measurements over a four-week period demonstrated significant increases in tumor size for CA scaffold pre-cultured HCC cells compared to both 2D and Matrigel pre-cultured HCC cells (FIGS. 12A and 12B). CA pre-cultured PLC cells generated final in vivo tumor volumes nearly twice as large as that generated by PCL cells pre-cultured in 2D or Matrigel, while maintaining consistent proliferation rates between pre-culture conditions (FIG. 12A). Statistically significant differences were observed between PLC cultured samples at 1 ($p<0.01$), 2 ($p<0.01$), 3 ($p<0.01$), and 4 ($p<0.01$) weeks. Similarly, CA pre-cultured HepG2 cells expanded to form tumors over four times the size of 2D cultured cells, and significantly larger than those pre-cultured in Matrigel, again maintaining consistent proliferation rates for this cell line (FIG. 12B), with statistically significant differences between samples at the 2 ($p<0.01$), 4 ($p<0.01$), 6 ($p<0.01$) and 8 ($p<0.01$) week time points as well. The CA pre-cultured cells effected favorable conditions for tumor expansion in vivo without altering expansion rates for either HCC cell line.

Figure 13A:
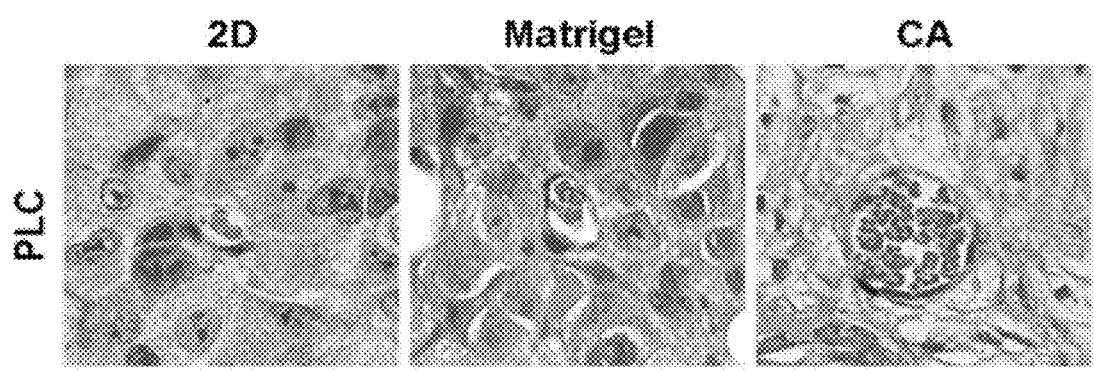
FIGS. 13A and 13B are images comparing hematoxylin and eosin stained histological sections of tumors induced by implanted (13A) PLC and (13B) HepG2 cells pre-cultured on 2D tissue culture plates, Matrigel matrices, and CA scaffolds, respectively. The implants were harvested 4 weeks post implantation in nude mice. Nuclei are stained dark purple, cytoplasm is stained light red, erythrocytes are stained bright red, and connective tissue is stained pink. Arrows indicate extravascular erythrocytes. The scale bar represents 20 µm.
Figure 13B:
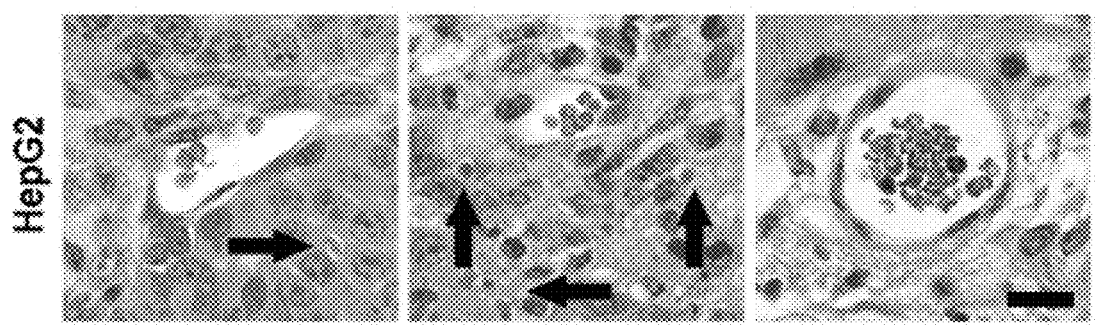

Tumors were harvested 4 weeks post-implantation, formalin-fixed, and sectioned for histological imaging. Hematoxylin and eosin staining revealed significant differences in blood vessel morphology based on pre-culture condition (FIGS. 13A and 13B). Both 2D and Matrigel pre-cultured cells displayed consistently small and irregularly shaped blood vessels with poorly endothelialized thin walls which did not consistently delineate the vessel from the surrounding tissue. In contrast, CA pre-cultured cells induced the formation of large, well rounded blood vessels with well-defined endothelial linings, carrying large numbers of erythrocytes. Additionally, the original porous structure of the CA scaffold was not observed in the histological samples, indicating the scaffold is completely removed by the remodeling action of the cells, confirming the scaffold's excellent biodegradability.

Cellular Response to Chemotherapy

Figure 14A:
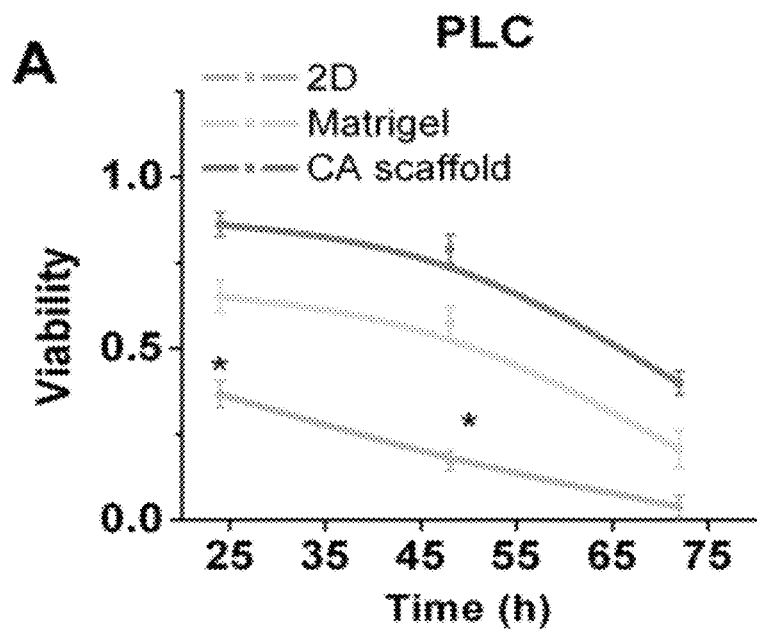
FIGS. 14A and 14B compare drug resistance of hepatocellular carcinoma cells cultured under different conditions. Viability of (14A) PCL and (14B) HepG2 cells cultured on 2D tissue culture plates, Matrigel matrices, and CA scaffolds, respectively, relative to untreated cells, as determined by the Alamar Blue assay after doxorubicin treatment. PLC cells were treated with 5 µM doxorubicin and HepG2 cells were treated with 10 µM doxorubicin. Results are mean±s.d., and * indicates at least one of the group means is statistically different from the others at that time point, p<0.05, n=4.
Figure 14B:
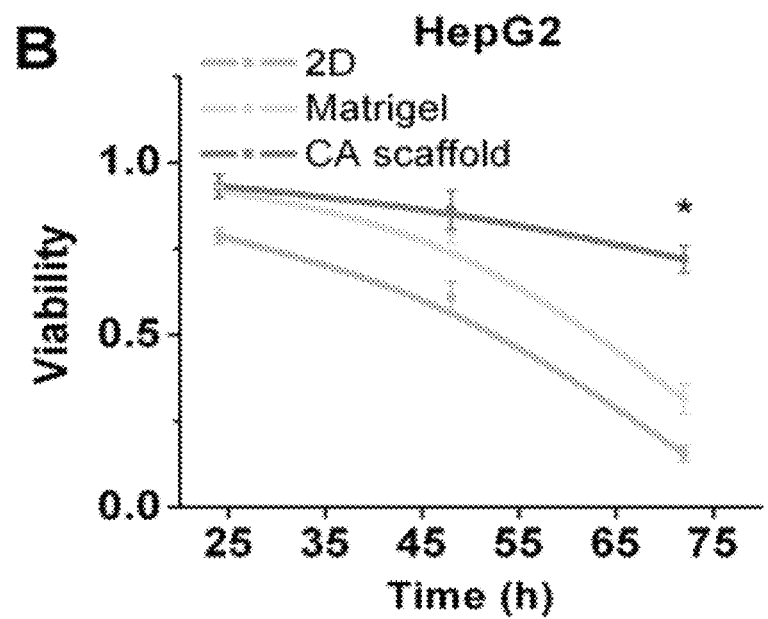
Figure 15A:
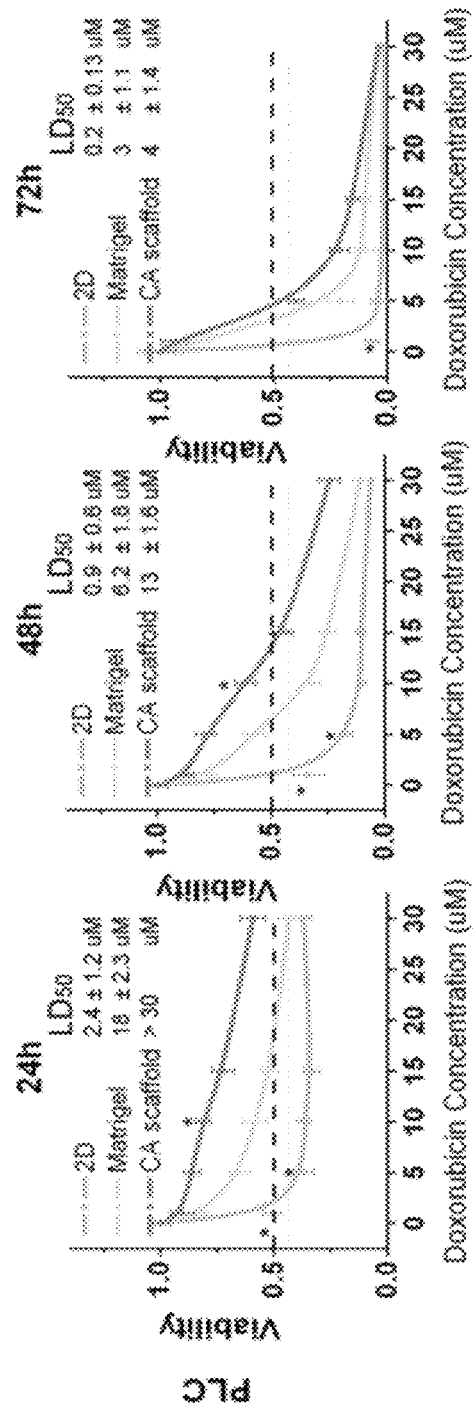
FIGS. 15A and 15B compare dose-dependent cytotoxic response of hepatocellular carcinoma cells to doxorubicin.
Figure 15B:
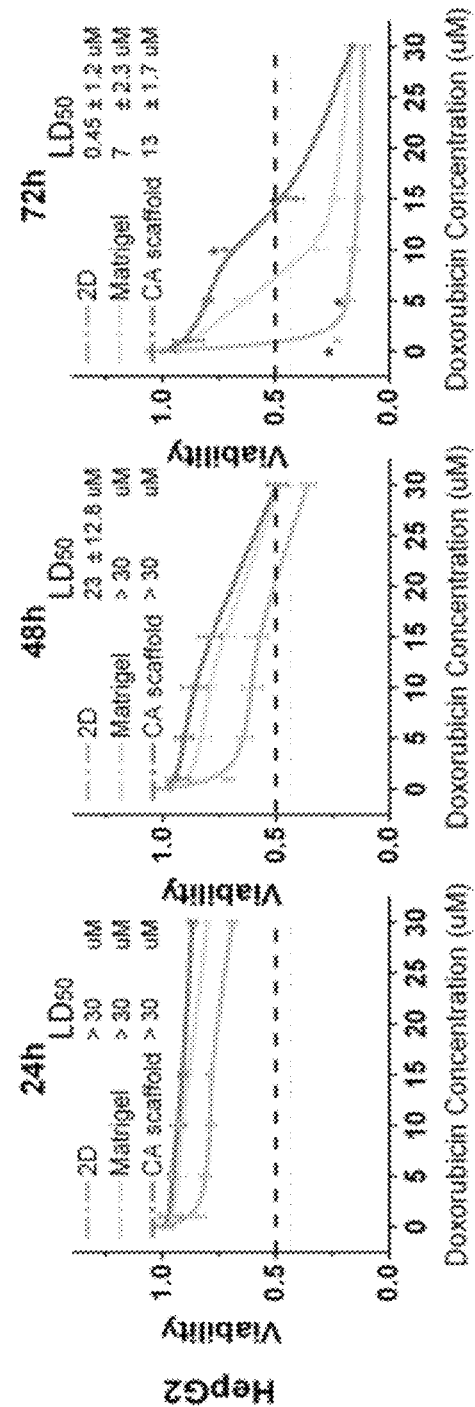

To determine if the in vitro microenvironment is capable of inducing an environment-mediated drug response in the tumor models, cell viability in response to doxorubicin treatment was evaluated. Cell viability was then assessed over a 72-hour period using the Alamar Blue assay (FIGS. 14A, 14B, 15A, and 15B). Successive viability measurements of doxorubicin treated cells revealed significantly different cytotoxic responses between cell types and culture conditions (FIGS. 14A and 14B). PLC cell viability declined rapidly in 2D culture, with statistically significant differences in cell viability observed at 24 hours ($p<0.01$) and 48 hours ($p<0.01$) after treatment between culture conditions when treated with 5 μM doxorubicin (FIG. 14A). After 24 hours of drug induction, a differential, dose-dependent survival response was observed where viability of 2D cultured PLC cells was significantly lower than either Matrigel or CA cultured cells after treatment with 1 μM ($p<0.01$), 5 μM ($p<0.01$), and 10 μM ($p<0.01$) doxorubicin (FIG. 15A). At 48 hours, differences in the survival of PLC cells based on culture condition became more apparent, and viability of CA cultured cells was also observed to be significantly higher than other culture models in 1 μM ($p<0.01$), 5 μM ($p<0.01$), and 10 μM ($p<0.01$) doxorubicin treatments (FIG. 15A). Finally, significant differences in PLC viability between culture conditions was observed 72 hours after 1 μM ($p<0.01$) doxorubicin treatment (FIG. 15A). In a similar fashion, HepG2 cells also responded differentially to doxorubicin dose over time. Differences in HepG2 viability between cell culture conditions were not apparent until 72 hours post treatment ($p<0.01$) when treated with 10 μM doxorubicin (FIG. 14B). While the onset of cell death in HepG2 cells was much less pronounced at 24 and 48 hours compared to PLC cells, the viability was notably decreased in 2D cultures compared to both Matrigel and CA 3D cultures, statistically significant differences observed in HepG2 viability observed at 72 hours when treated with 1 μM ($p<0.01$), 5 μM ($p<0.01$), and 10 μM ($p<0.01$) doxorubicin (FIG. 15B). Interestingly, at 72 hours, the viability of HepG2 cells cultured on CA scaffolds and exposed to 1 μM doxorubicin increased slightly to 88.6±2.75% compared to 86.7±2.4% at 48 hours (FIG. 15B). The viability measurements indicated that a population of HepG2 cells cultured in CA scaffolds had survived doxorubicin treatment that had eliminated cells cultured on 2D plates.

The $LD_{50}$ of a drug is defined as the median lethal dose and commonly used as a measure of the effectiveness of a drug in inhibiting biological or biochemical function. The $LD_{50}$ of doxorubicin in each of the conditions was evaluated post induction, where both HCC cell types displayed significant differences in cell viability across culture conditions (FIGS. 15A and 15B). The $LD_{50}$ of doxorubicin was 0.2±0.13 μM for PLC cells cultured on 2D surfaces, 3±1.1 μM for Matrigel cultured, and 4±1.4 μM CA cultured cells as determined at 72 hours post treatment (FIG. 15A). Similarly, the $LD_{50}$ for doxorubicin treated HepG2 cells cultured in 2D substrate was 0.45±0.18 μM, increasing to 7±2.2 μM in Matrigel, and finally to 13±1.7 μM in CA at 72 hours post treatment (FIG. 15B).

The microenvironment conditions produced in the CA tumor models induced significant changes in cellular behavior as compared to conventional 2D culture environments. Doxorubicin is an anthracyline antibiotic that induces apoptosis in HCC by intercalating DNA and interfering with topoisomerase II DNA replication. Doxorubicin is a cytotoxic agent commonly incorporated in catheter-based therapies for metastatic disease, ideal for measuring and comparing response of systemic therapies against HCC. 2D, Matrigel, and CA scaffold cultured HCC cells were treated with doxorubicin supplemented media for 24 hours at a physiologically relevant dose based on the clearance rate of doxorubicin in vivo. Overall, CA cultured cells exhibited significantly greater viability than either 2D or Matrigel cultured cells when exposed to doxorubicin, suggesting that the CA microenvironment induced greater resistance to chemotherapy. The $LD_{50}$ for doxorubicin treated PLC cells increased significantly, by nearly twenty times in 3D culture compared to 2D culture, and for HepG2, tumor models formed in CA scaffolds had an $LD_{50}$ nearly thirty times greater than 2D cultured cells. The tumor cell clusters that formed exclusively upon culture in CA scaffolds reduced the exposure of the cells to therapeutic agents because diffusion of therapeutic agents into the tumor mass is limited by the distance of the core to the supply, and may induce drug resistant properties typical to spheroid culture. The upregulation of the P-glycoprotein multidrug transporter, strongly linked to doxorubicin resistance, has been associated with the 3D tumor microenvironment and also likely contributed to observed doxorubicin resistance. Additionally, hypoxic conditions at the core of the tumor cluster may trigger cell quiescence, making these cells less susceptible to the action of doxorubicin that interrupts the cell cycle during DNA replication. This was confirmed by the elevated levels of bFGF and VEGF expression, which have been associated with intercalating agent resistant quiescent tumor phenotypes, in CA HCC tumor models. Finally, GPC-3 over-expression, which has been implicated in the increased resistance to topoisomerase II inhibitors such as doxorubicin, was displayed by HepG2 cells cultured in CA scaffolds. The greatly increased resistance of 3D CA HCC tumor models to chemotherapy more closely resembles the in vivo levels of resistance, where standard dosing schemes result in peak plasma concentrations of approximately 15 μM doxorubicin minutes after treatment, declining to nearly complete clearance at 48 hours post treatment. The CA scaffolds were shown to be capable of stimulating cooperative signaling between cells and the environment that led to the expression of a highly malignant, drug resistant phenotype.

The following examples are provided for the purpose of illustrating, not limiting, the invention.

EXAMPLES

Materials and Methods

Materials.

All chemicals were purchased from Sigma-Aldrich (St. Louis, Mo.) unless otherwise specified. Chitosan (Poly-Sciences, Pa., 15,000 MW) and sodium alginate powders were used as received. Antibiotic-antimycotic, Dulbecco's Modified Eagle Medium (DMEM), Antibiotic-antimycotic, Dulbecco's phosphate buffered saline (D-PBS), and Alamar Blue reagent were purchased from Invitrogen (Carlsbad, Calif.). Fetal bovine serum (FBS) was purchased from Atlanta Biologicals (Atlanta, Ga.). C6 rat glioma, U-87 MG human glioma, and U-118 MG human glioma cell lines, and PLC/PRF/5 (PLC) and HepG2 human hepatocellular carcinoma cell lines, and Minimum Essential Media (MEM) were purchased from American Type Culture Collection (ATCC, Manassas, Va.). Cells were maintained according to manufacturer's instructions in fully supplemented DMEM (C6 and U-118 MG) or MEM (U-87 MG) with 10% FBS and 1% antibiotic-antimycotic) at 37° C. and 5% $CO_2$ in a fully humidified incubator. Reduced growth factor Matrigel matrix was purchased from BD Biosciences (San Jose, Calif.). VEGF and MMP-2 ELISA kits were purchased from R&D Systems (Minneapolis, Minn.). PVDF membrane and Immun-star chemiluminescent reagent for dot blotting were purchased from BioRad (Hercules, Calif.), while antibodies were purchased from Abcam (Cambridge, Mass.).

Cell Proliferation Analysis.

Proliferation of cells cultured on 2D wells, Matrigel matrix, and CA scaffolds was determined using the Alamar Blue assay following the manufacturer's protocol. Briefly, cells cultured on 2D wells and 3D scaffolds were washed with D-PBS before adding 1 mL of Alamar Blue solution (10% Alamar Blue in fully supplemented phenol red free DMEM or MEM) to each well.

For glioma cells, after 1.5 hrs the Alamar Blue solution was transferred to a 96-well plate to obtain absorbance values on a microplate reader. The cell number was calculated based on standard curves created previously. Cells were again washed with D-PBS to remove Alamar Blue solution and fresh fully supplemented media was added to each well.

For human hepatocellular carcinoma cells, after 2 hrs the Alamar Blue solution was transferred to a 96-well plate to obtain fluorescent values on a SpectraMax M2 microplate reader (Molecular Devices, Sunnyvale, Calif.) at 550 nm excitation, 590 nm emission. Standard curves were generated by seeding cells counted using a hemocytometer onto cell culture materials in triplicate, and performing Alamar Blue assay to generate a plot of linear regression of fluorescent values vs. cell number for each material. The cell number in an experimental sample was calculated based on the standard curve. No background fluorescence was generated by CA scaffolds. Cells were again washed with D-PBS to remove Alamar Blue solution and fresh fully-supplemented media were added to each well.

Cellular Morphology Analysis by SEM.

Samples for SEM analysis were first fixed with cold Karnovsky's fixative overnight followed by dehydration in a series of ethanol washes (0%, 50%, 75%, 90%, 100%). Samples were critical point dried and sputter coated with platinum before imaging with a JSM 7000 SEM (JEOL, Tokyo, Japan). False color was added to SEM images using Adobe Photoshop in order to improve the contrast between cells and substrate.

Growth Factor and Extracellular Matrix Secretion Analysis.

After 7 and 9 days of culture for C6 and both U-87 MG and U-118 MG cells, respectively, media of differently cultured cells were replaced with a low serum counterpart (media containing 1% FBS and 1% antibiotic-antimycotic) and cells were incubated for 24 hrs. Media were collected and stored at −80° C. for future use. VEGF and MMP-2 secretion was determined following the manufacturer's protocol, protein concentration per cell was calculated based on cell number in the well, and the values were normalized to 2D culture conditions. Laminin and fibronectin were detected using dot blot analyses and protein concentration per cell was normalized to 2D culture conditions using ImageJ.

For human hepatocellular carcinoma cells, after 9 days of culture, media from cell cultures were replaced with a low serum counterpart (media containing 1% FBS and 1% antibiotic-antimycotic) and cells were incubated for 24 hrs. Media were collected and stored at −80° C. for future use. Growth factor (bFGF, IL-8, and VEGF) secretion was determined via ELISA assays following the manufacturer's protocol. The protein concentration per cell was calculated based on cell number in the well, and the values were normalized to 2D culture conditions. Glypican-3 was detected using dot blot analysis and protein concentration per cell was normalized to 2D culture conditions using ImageJ (NIH, Bethesda, Md.).

In Vivo Studies.

All animal studies were performed in accordance with University of Washington IACUC approved protocols. Athymic nude male mice (nu/nu, 088 strain, Charles River, Wilmington, Mass.) 6-8 weeks of age were anesthetized with a solution of ketamine and xylazine before CA scaffolds containing cells were implanted subcutaneously into the left and right flank. 2D and Matrigel matrix pre-treated cells were diluted into 100 μL media to a cell number matching that on the CA scaffolds as determined by Alamar Blue assay, and mixed with 100 μL Matrigel before injecting subcutaneously into the left and right flanks of the anesthetized mice.

For gliomas cell-containing scaffolds, tumors were measured using calipers and the volume was calculated using the formula of a cylinder, volume=length×width×height×π/4, for CA scaffold tumors (cell-CA scaffold construct has an cylindrical shape), and using the formula for the volume of an ellipsoid, volume=length×(width$^2$)×π/6, for 2D and Matrigel tumors. CA scaffold tumor sizes were normalized by subtracting the volume of an empty scaffold (265 mm$^3$) from the calculated tumor volume. After 3 weeks and 4 weeks of implantation for C6 and U-87 MG tumors, respectively, mice were sacrificed by $CO_2$ inhalation followed by cervical dislocation, and the tumors were resected, fixed in a 10% formalin solution, and submitted for histological analyses.

For human hepatocellular carcinoma cell-containing scaffolds, four mice were tested per group. CA scaffold tumors were measured using calipers and volume was calculated using the formula of a cylinder, i.e., volume=radius$^2$×height×π, subtracting initial dimensions of the scaffold (265 mm$^3$), and the formula for an ellipsoid volume (22) (volume=length×width$^2$×π/6) was used for 2D and Matrigel tumors. 4 weeks post-implantation of PLC and HepG2 tumors, mice were sacrificed by $CO_2$ inhalation followed by cervical dislocation, and the tumors were resected, fixed in a 10% formalin solution, and submitted for histological analyses.

Immunohistochemistry.

Excised tumors were embedded in optimal cutting temperature (OCT) compound and frozen on dry ice. The frozen tumor tissue sections (8 μm) were washed thrice with PBS to remove excess OCT compound and fixed for 10 min in formaldehyde. $CD31^+$ cells were stained with an anti-mouse CD31 primary antibody (Abcam, Cambridge, Mass.) and visualized with an anti-goat IgG FITC conjugated secondary antibody (Abcam, Cambridge, Mass.) following the manufacturer's protocol. The slides were counterstained with 4',6-diamidino-2-phenylindole (DAPI) in mounting medium (ProLong Gold, Invitrogen, Carlsbad, Calif.) and imaged using a Zeiss LSM 510 confocal microscope.

Cellular Response to Chemotherapeutic Agents.

For human hepatocellular carcinoma cell-containing scaffolds, after 10 days of culture, media from cell cultures were replaced with 1 mL fully supplemented cell culture media containing various concentrations of doxorubicin. Cells were induced with doxorubicin containing media for 24 h, after which media was replaced with standard fully supplemented cell culture media. Cell viability was assessed using the Alamar Blue assay following the manufacturer's protocol as described above. $LD_{50}$ was estimated via a polynomial approximation.

Statistical Analysis.

Acquired data are expressed as mean±SD. Statistical significance was determined by one-way analysis of variance (ANOVA) and Student's t test. Values of P<0.01 were considered significant.

For cellular response to chemotherapeutics, all experiments were performed in quadruplicate (n=4). Data are presented as means±standard deviation. Statistical analysis at each sampling point was performed using one-way analysis of variance (ANOVA) comparing each treatment condition. Differences were considered significant for p<0.05.

Example 1

The Preparation and Seeding of a Representative Chitosan-Alginate Scaffold

Chitosan-alginate (Calif.) scaffolds were prepared as described in Li Z., Ramay H. R., Hauch K. D., Xiao D., Zhang M. Chitosan-alginate hybrid scaffolds for bone tissue engineering, Biomaterials 2005, 26:3919-3928; Li Z., Zhang M. Chitosan-alginate as scaffolding material for cartilage tissue engineering, J Biomed Mater Res A 2005, 75:485-493; and U.S. Pat. No. 7,736,669, expressly incorporated herein by reference in its entirety.

Briefly, a 4 wt % chitosan and 2 wt % acetic acid solution was mixed under constant stirring in a blender for 7 minutes to obtain a homogeneous chitosan solution. A 4 wt % alginate solution was added to the chitosan solution, and mixed in a blender for 5 min to obtain a homogeneous CA solution. The CA solution was cast in 24-well cell culture plates and frozen at −20° C. for 8 hrs. The samples were then lyophilized, optionally sectioned into disks of 13 mm diameter×2 mm thickness, crosslinked in 0.2 M $CaCl_2$ solution for 10 minutes under vacuum, washed with deionized water several times to remove any excess salt, and sterilized in 70 v % ethanol for 1 hr. The scaffolds were then transferred to a sterile PBS solution and placed on an orbital shaker for about 12 hrs to remove any excess ethanol.

Cells were seeded onto PBS damp CA scaffolds in 24-well plates at 50,000 cells per scaffold in 50 µL fully supplemented media. Cells were allowed to infiltrate the scaffold for 1 hr before 1 mL fully supplemented media was added to each well. For Matrigel pre-cultured samples, 50,000 cells in 200 µL fully supplemented media was mixed with 200 µL Growth Factor Reduced Matrigel matrix to form a viscous liquid and added to 24-well plate wells to gel in situ. Samples were allowed to gel for 1 hr before 1 mL fully supplemented media was added to each well. For 2D pre-cultured samples, 50,000 cells in 1 mL fully supplemented media were added to 24-well plate wells. Media were replaced every 2 days.

While illustrative embodiments have been illustrated and described, it will be appreciated that various changes can be made therein without departing from the spirit and scope of the invention.

The embodiments of the invention in which an exclusive property or privilege is claimed are defined as follows:

1. A three-dimensional scaffold, comprising:
(a) a porous chitosan-alginate scaffold; and
(b) cultured cancer cells,
wherein the cancer cells are seeded on the scaffold and are cultured for a time sufficient to produce tumor spheroids.

2. The scaffold of claim 1, wherein the cultured cancer cells have increased tumor malignancy compared to two-dimensionally cultured cancer cells.

3. The scaffold of claim 1, wherein the cultured cancer cells have increased expression of growth factors compared to two-dimensionally cultured cancer cells.

4. The scaffold of claim 1, wherein the cultured cancer cells have increased expression of the enzyme MMP-2 compared to two-dimensionally cultured cancer cells.

5. The scaffold of claim 1, wherein the cultured cancer cells have increased expression of the extracellular matrix proteins compared to two-dimensionally cultured cancer cells.

6. The scaffold of claim 1, wherein the cultured cancer cells have increased tumorigenicity in vivo compared to two-dimensionally cultured cancer cells.

7. The scaffold of claim 1, wherein the cultured cancer cells have increased $CD31^+$ cell recruitment in vivo compared to two-dimensionally cultured cancer cells.

8. A method for producing a cancerous tumor in a subject, comprising implanting in a subject the scaffold of claim 1, and growing the cancer cells for a sufficient amount of time to produce a cancerous tumor in said subject.

9. A method for screening a candidate chemotherapeutic agent in vitro comprising contacting in vitro the scaffold of claim 1 with a candidate chemotherapeutic agent and measuring growth of the cancer cells, wherein a decrease in growth of said cancer cells in said scaffold as compared to a control identifies said agent as a chemotherapeutic agent.

10. The method of claim 9, wherein measuring growth of the cancer cells comprises measuring cell proliferation or measuring cell viability in said cancer cells.

11. A method for screening a candidate chemotherapeutic agent in vivo comprising: (a) implanting in a subject the scaffold of claim 1; (b) administering a candidate chemotherapeutic agent to said subject; and (c) measuring growth of the cancer cells, wherein a decrease in growth of said cancer cells in said scaffold as compared to a control identifies said agent as a chemotherapeutic agent.

12. The method of claim 11, wherein prior to administering the candidate chemotherapeutic agent to said subject the cancer cells of said scaffold grow for a sufficient amount of time to produce a tumor; wherein said measuring growth of the cancer cells encompasses measuring mass or volume of the tumor both prior to and after administering the candidate chemotherapeutic agent; and wherein said control is the measured mass or volume of the tumor prior to administering the candidate chemotherapeutic agent.

* * * * *